US005885225A

United States Patent [19]
Keefe et al.

[11] Patent Number: 5,885,225
[45] Date of Patent: Mar. 23, 1999

[54] SYSTEM AND METHOD FOR THE MEASUREMENT OF EVOKED OTOACOUSTIC EMISSIONS

[75] Inventors: Douglas H. Keefe, Omaha, Nebr.; Robert Ling, Mercer Island, Wash.

[73] Assignee: Boys Town National Research Hospital, Omaha, Nebr.

[21] Appl. No.: 599,467

[22] Filed: Jan. 23, 1996

[51] Int. Cl.$^6$ .................................................. A61B 5/00
[52] U.S. Cl. .......................................... 600/559; 73/585
[58] Field of Search .................................. 128/746, 848; 73/585; 600/559, 552

[56] References Cited

U.S. PATENT DOCUMENTS

| | | | |
|---|---|---|---|
| 4,374,526 | 2/1983 | Kemp | 128/746 |
| 4,884,447 | 12/1989 | Kemp | 73/585 |
| 5,413,114 | 5/1995 | Zurek et al. | 128/746 |
| 5,526,819 | 6/1996 | Lonsbury-Martin et al. | 128/746 |
| 5,546,956 | 8/1996 | Thornton | 128/746 |
| 5,594,174 | 1/1997 | Keefe | 128/746 X |

*Primary Examiner*—Francis J. Jaworski
*Attorney, Agent, or Firm*—Henderson & Sturm

[57] ABSTRACT

A system and method for using double-evoked otoacoustic emission (2EOAE) signals to elicit an evoked response from the cochlea. A three sample stimulus includes a first signal, a time delayed second signal and the superposition of the first and second signals. The time delay is selected to be less than the maximum latency of the cochlear emission. Each of the three signals elicits a response from the cochlea that include a linear response. The linear response is eliminated by subtracting the response to the first and second individual signals from the response to the superposition signal. One class of signals arises when the time delayed signal is a scaled version of the first signal. The signals can include click signals, chirp signal and the like. Chirp signals can be used to mimic classical distortion product (DP) responses. The signals may be presented using a single acoustic source or separate acoustic sources. With the appropriate selection of time delays, the 3 signal stimulus can greatly reduce nonlinear response due to probe distortion. With two acoustic sources, probe distortion can be virtually eliminated. The system also includes a noise coherence measurement to determine the relative levels of system response caused by random noise as opposed to nonlinear response. A real-time artifact rejection technique also simplifies the collection of data.

39 Claims, 12 Drawing Sheets

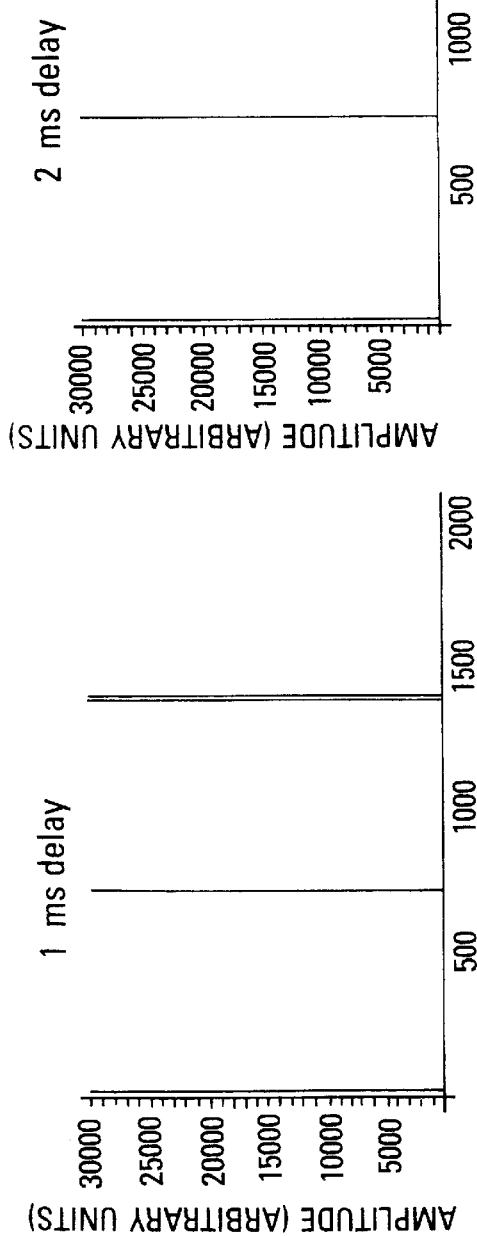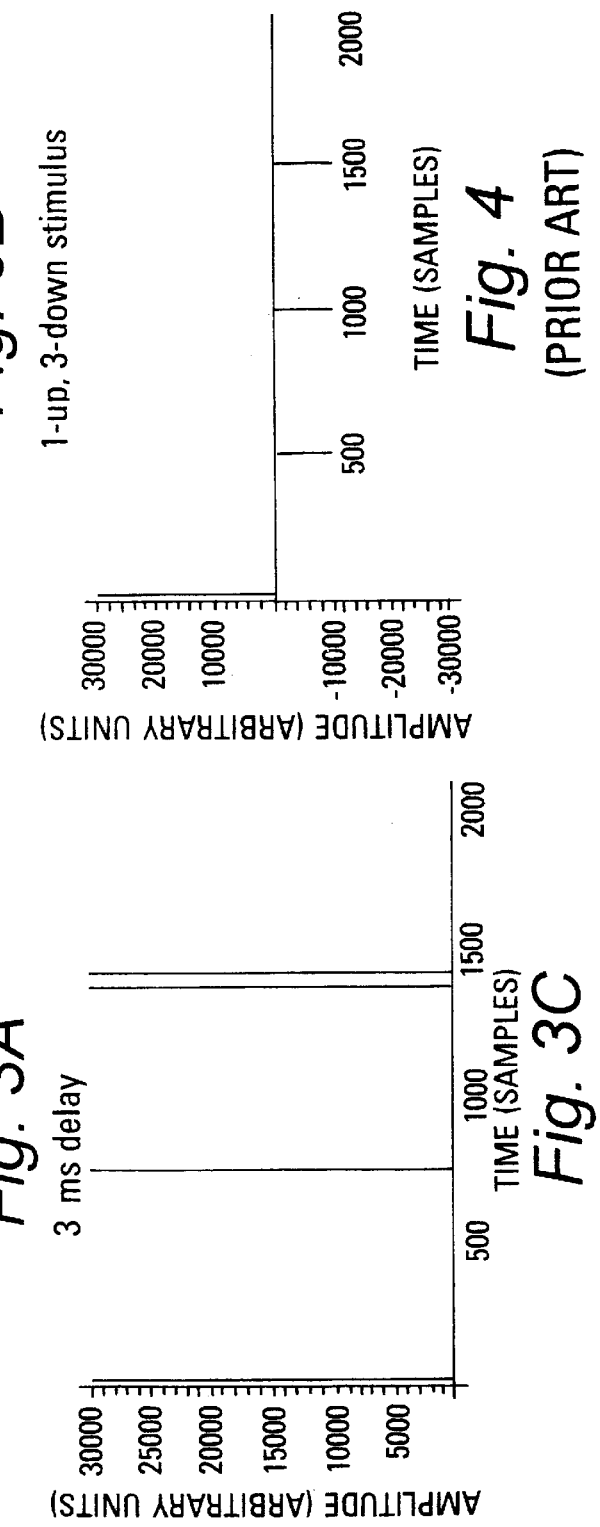

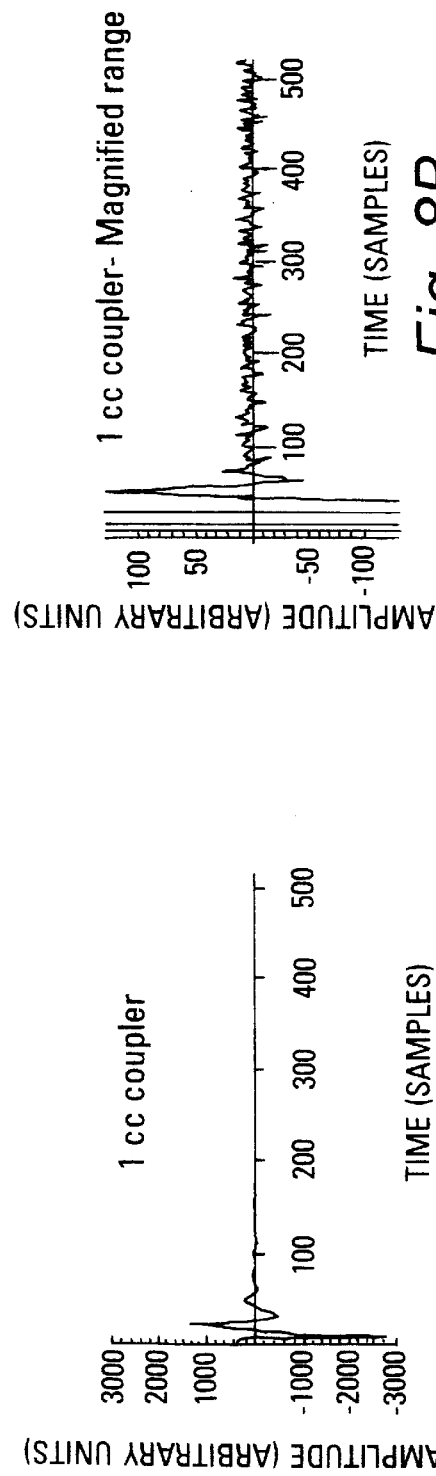
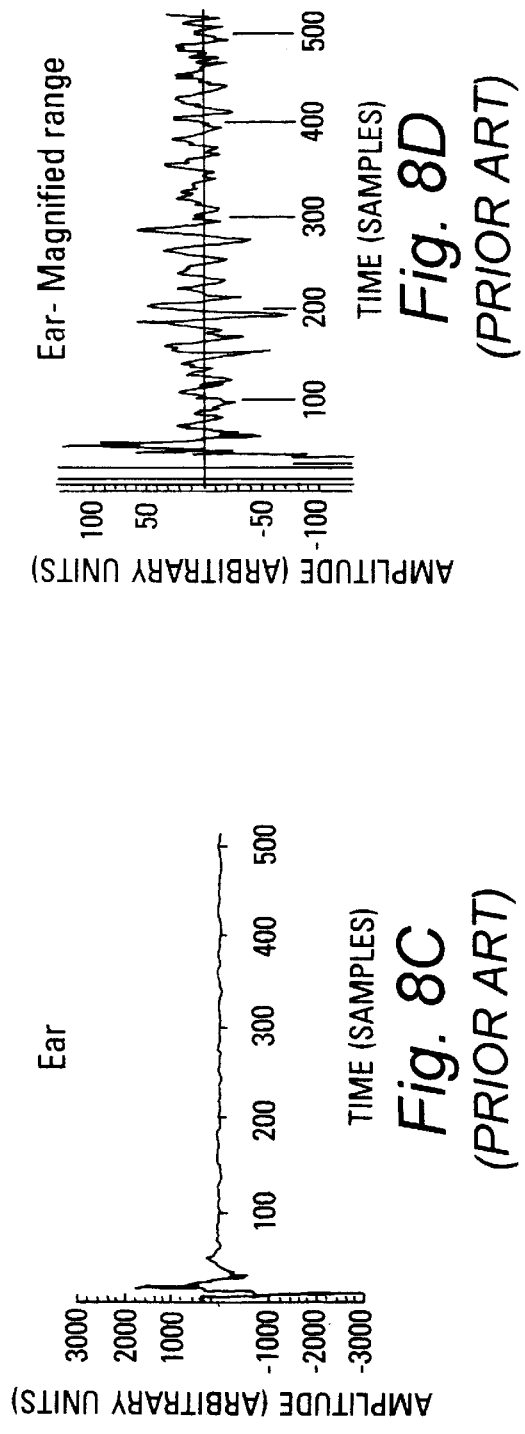
Fig. 8A (PRIOR ART)
Fig. 8B (PRIOR ART)
Fig. 8C (PRIOR ART)
Fig. 8D (PRIOR ART)

1/3 - octave averaged
Ear response (upper curves) and 1-cc coupler response (lower curves)
Signal: solid line
Signal +/- Noise: dashed line 1 ms delay 2 ms delay 3 ms delay Total responses--response to stimulus s1
2CEOAE responses-nonlinear response with zero time delay between s1 and s2
Noise responses-random noise calculated from nonlinear coherence

SYSTEM AND METHOD FOR THE MEASUREMENT OF EVOKED OTOACOUSTIC EMISSIONS

TECHNICAL FIELD

The present invention is related generally to the field of evoked otoacoustic emissions, and, more particularly, to a system and method for measuring evoked otoacoustic emissions.

BACKGROUND OF THE INVENTION

Cochlear response measurements in the ear canal pre-date the discovery of otoacoustic emissions. The importance of measurements of the acoustic impedance of the ear from a location in the ear canal has been long known, beginning with measurements obtained in 1928 and described in "Measurement of the Acoustical Impedances of Human Ears," by W. West, *Post Office Electrical Engineers Journal*, 21:293–300, 1928. Subsequent research has led to techniques that provide information on the external, middle and inner ear. One such system, described in U.S. Pat. No. 3,294,193, issued 1966 to Zwislocki, describes an instrument that measures a response function of the ear.

A subset of this response function provides measurements of reflected energy from the cochlea, because the mid-frequency part of the resistive component of the middle ear impedance is mainly due to the cochlear resistance, as first obtained by measurements in cats and rabbits, as described in "An Experimental Study of the Acoustic Impedance of the Middle Ear and its Transmission Properties," A. Moller, *Acta Oto-Laryngol.*, 60:129–149, 1965, and *Auditory Physiology*, A. Moller, Academic Press, New York, 1983.

Early research had established the cochlear origin of subharmonic distortion products recorded in ear-canal pressure response measurements, as described in "On the Generation of Odd-Fractional Subharmonics," P. Dallos, *J. Acousi. Soc. Am.*, 40:1382–1391, 1966, and in *The Auditory Periphery*, P. Dallos, Academic Press, U.S.A., 1973. Dallos also commented on his early research into the source of acoustic emissions in Comment on 'Observations on the Generator Mechanism of Stimulus Frequency Acoustic Emissions-Two Tone Suppression' (D. T. Kemp and R. Chum) in *Psychophysical, Physiological and Behavioral Studies in Hearing*, page 42, E. deBoer and M. A. Viergever, editors, Delft University Press, 1980.

Following this early work by Dallos, otoacoustic emissions (OAEs) were discovered by D. Kemp, described in "Stimulated Acoustic Emissions From Within the Human Auditory System," D. T. Kemp, *J. Acoust. Soc. Am.*, 64:1386–1391, 1978. Kemp's discoveries initiated an active period of research continuing to the present on cochlear-based signals that are inferred from pressure measurements in the ear canal. Broadly speaking, OAEs are classified into spontaneous otoacoustic emissions (SOAE), which refer to cochlear-based responses in the ear canal in the absence of any external stimulus, and evoked otoacoustic emissions (EOAE), which arise in response to an acoustic stimulus delivered into the ear canal.

These evoked responses are categorized according to the type of stimulus. The stimulus-frequency otoacoustic emission (SFOAE) is obtained using a sinusoidal signal, as described in "Observations on the Generator Mechanism of Stimulus Frequency Acoustic Emissions-Two Tone Suppression," D. T. Kemp and R. Chum, in *Psychophysical, Physiological and Behavioral Studies in Hearing*, pages 34–41, E. deBoer and M. A. Viergever, editors, Delft University Press, 1980. The SFOAE is a low-level signal measured in the ear canal at the frequency of the sine tone, which is based upon the property that the evoked emission has a saturating nonlinearity as the stimulus level is increased.

Other types of stimulus signals include a click-evoked otoacoustic emission (CEOAE) response, described in "Stimulated Acoustic Emissions From Within the Human Auditory System," *J. Acoust. Soc. Am.*, 64:1386–1391, 1978, U.K. Provisional Patent No. 5467/78, 1978 to D. T. Kemp, U.S. Pat. No. 4,374,526, issued Feb. 22, 1983 to Kemp ("Kemp (1983)"), and U.S. Pat. No. 4,884,447, issued Dec. 1, 1989 to Kemp ("Kemp (1989)"). These references describe a measurement that is the pressure response to the presentation of a single click (also termed pulse), or the differential pressure response pulse to the presentation of clicks delivered at two (or more) intensity levels. A click, or, equivalently, a pulse, is a wide-bandwidth, deterministic, short-duration signal. The duration is usually limited by the duration of the impulse response of the acoustic source transducer, since the electrical input signal to the source transducer is typically much shorter than this impulse response duration. The stimulus duration is typically 1–4 milliseconds (msec), whereas the overall duration of the CEOAE response is in the range of 10–40 msec. In the prior art of Kemp (1983), the duration of the CEOAE response is assumed to extend over a 20 msec interval, and to prevent overlapping of the responses from succeeding pulse stimuli, it is stated that the time interval between pulses should be at least 20 msec, corresponding to a presentation rate of 50 Hz. Time gating of the response is recommended to remove the initial 5 msec of the total response, which is not included in the definition of the OAE response, and this initial portion of the response is thus excluded from the definition of the CEOAE response.

Distortion product otoacoustic emissions (DPOAEs or DPs) are OAEs measured in response to a stimulus comprised of two continuous, sinusoidal tones with frequencies $f_1$ and $f_2$. Information from the DPOAE includes the frequencies at which there are significant intensity levels, for example, at the $2f_1-f_2$ DP site. The term "site" refers to the location in the cochlea that is believed to generate the evoked emission. The underlying cochlear mechanisms leading to latencies or time delays in CEOAE also produce latencies in the DPOAE responses, which can be measured in terms of the group delay, as can be appreciated by those skilled in the art, and interpreted to provide information on cochlear micromechanics. The term "latency" refers to the time delay in the evoked response to the stimulus, whereas the group delay is defined based upon the rate of change of the signal phase with frequency. To control for probe nonlinearity, it is typical to use two source probes. One probe outputs the sine tone at $f_1$, and the other probe outputs the sine tone at $f_2$. The use of two independent probes controls for the intermodulation distortion that would otherwise occur at sum and difference frequencies if a single probe were used.

As described in "A Review of Otoacoustic Emissions." R. Probst, B. L. Lonsbury-Martin, and G. K. Martin, *J. Acoust. Soc. Am.* 89:2027–2067, 1991, current research indicates that these various OAE measurements systems are providing information from a common physiological origin, involving cochlear micromechanics and the mechanisms underlying signal transduction in the cochlea. Thus, advances in EOAE measurement techniques are aimed at providing more accurate, or more comprehensive, data regarding these cochlear mechanisms.

More complex stimuli have been used to measure EOAEs, including tone bursts created using short-duration, rectangular-windowed sinusoids (other windows including Gaussian have been used). Time averaging of the evoked response with artifact rejection and noise rejection is recommended by Kemp et al. (1986). "Artifact rejection" in this prior art has been taken to include a differential subtraction of responses, so as to eliminate the linear response, as in Kemp (1989), including the use of time gating. "Noise rejection" in this prior art is when the sound pressure level (SPL) exceeds some threshold during the portion of the signal after the first 5 ms. This is taken as evidence of a noise source external to the cochlear response. Time averaging is effective at attenuating noise, but has no benefits for reducing the nonlinear response output by the probe that is synchronous with the stimulus presentation rate. Artifact rejection, as used in the present application, differs in meaning from that of Kemp (1989), and is defined below. This probe nonlinearity interacts with the middle ear response in the first few milliseconds after presentation of a click stimulus. Both the middle ear response and the probe nonlinearity are large during this time interval.

Different linear cancellation procedures have been utilized in an attempt to control for this probe nonlinearity. One approach measures two responses, a first response to the stimulus at one level and a second response to the same stimulus, but at some higher level, typically on the order of 6 decibels (dB) higher. The low-level response is boosted or amplified by the same difference in level (6 dB in this example), and subtracted from the high-level response. If the system were linear, then the result would be a null response. Thus, the measured response after subtraction is due to the EOAE response and the synchronous residual probe nonlinearity. The residual probe nonlinearity can be significant and contaminates the beginning of the EOAE response. To eliminate this initial contamination, the EOAE response is typically nulled over the first 2–5 msec. However, eliminating the beginning of the EOAE response results in the elimination of the high-frequency content of the EOAE which is characterized by short latencies in this range. Presently, no techniques exist for CEOAE or tone-burst EOAE systems to control for probe nonlinearity that are as effective as the two-source probe technique for the DPOAE measurements.

Another standard subtraction technique in CEOAE systems, discussed in Kemp (1989), uses a single probe to produce four stimuli. The first three stimuli are three identical clicks and the fourth stimuli is a fourth click, but with the opposite polarity and three times the amplitude of the first three identical stimuli. The responses are summed to produce a response which would be zero if the cochlear EOAE behaved as an ideal linear response. This subtraction of the linear response is the "artifact rejection" of Kemp et al. (1986). This is argued as reducing random noise, but the probe nonlinearity is not controlled, and is worse than the previously described technique since the relative gain between high and low-level clicks is larger, thereby producing greater amounts of probe distortion. The initial 5 msec of the CEOAE response is nulled to remove probe artifacts.

Each of the existing EOAE systems lacks the ability to easily measure a wideband response or suffers from the inability to control for probe nonlinearities. Therefore, it can be appreciated that there is a significant need for a system and method to measure stimuli to produce evoked emissions while controlling for nonlinearities without the use of time-gating. Moreover, present theories do not allow the interpretation of click-evoked OAE responses within the framework of a distortion product-evoked OAE response model, and vice versa. The present invention provides this and other advantages, as will be seen from the following discussion and accompanying figures.

SUMMARY OF THE INVENTION

The present invention is embodied in a system and method for measuring evoked otoacoustic emissions using a double-evoked otoacoustic emission stimulus and subtracting the responses in a manner that is nearly independent of probe distortion. In one embodiment the stimulus is a double click, while in another embodiment the stimulus signal is a double chirped signal. Signal processing techniques may be applied that unify the interpretation of otoacoustic emission responses in terms of the quick-evoked and distortion product-evoked models. In addition, a nonlinear coherence technique is used to separate the deterministic and random components of the response. A real-time artifact rejection technique permits the efficient extraction of the deterministic evoked response from noise.

BRIEF DESCRIPTION OF THE DRAWINGS

FIGS. 3A to 3C are waveforms illustrating the double-click evoked emission stimulus of the system of FIG. 1.

FIG. 4 is a waveform illustrating the conventional click evoked emission stimulus.

FIGS. 8A to 8D are waveforms of the evoked response to the conventional stimulus of FIG. 4.

DETAILED DESCRIPTION OF THE INVENTION

The present invention provides a system and method to measure Double-Evoked Otoacoustic Emissions (2EOAE), whose place of origin is the cochlea. Important sub-classes of 2EOAEs are Double-Chirp Distortion Products (2ChDP) and Double-Click-Evoked Otoacoustic Emissions (2CEOAE). The 2ChDP and 2CEOAE procedures have significant advantages over existing procedures. In particular, the new stimuli elicit new responses from the cochlea that provide additional information about the micromechanics of the inner ear. Furthermore, the new stimuli are generated in a manner that permits the control of probe nonlinearities and produce a new subtraction technique that is significantly better than conventional techniques for controlling probe distortion. The system of the present invention also permits the measurement of higher frequency responses, because the early-latency click-evoked OAE responses of the cochlea need not be nulled as is required by conventional systems.

Figure 1:
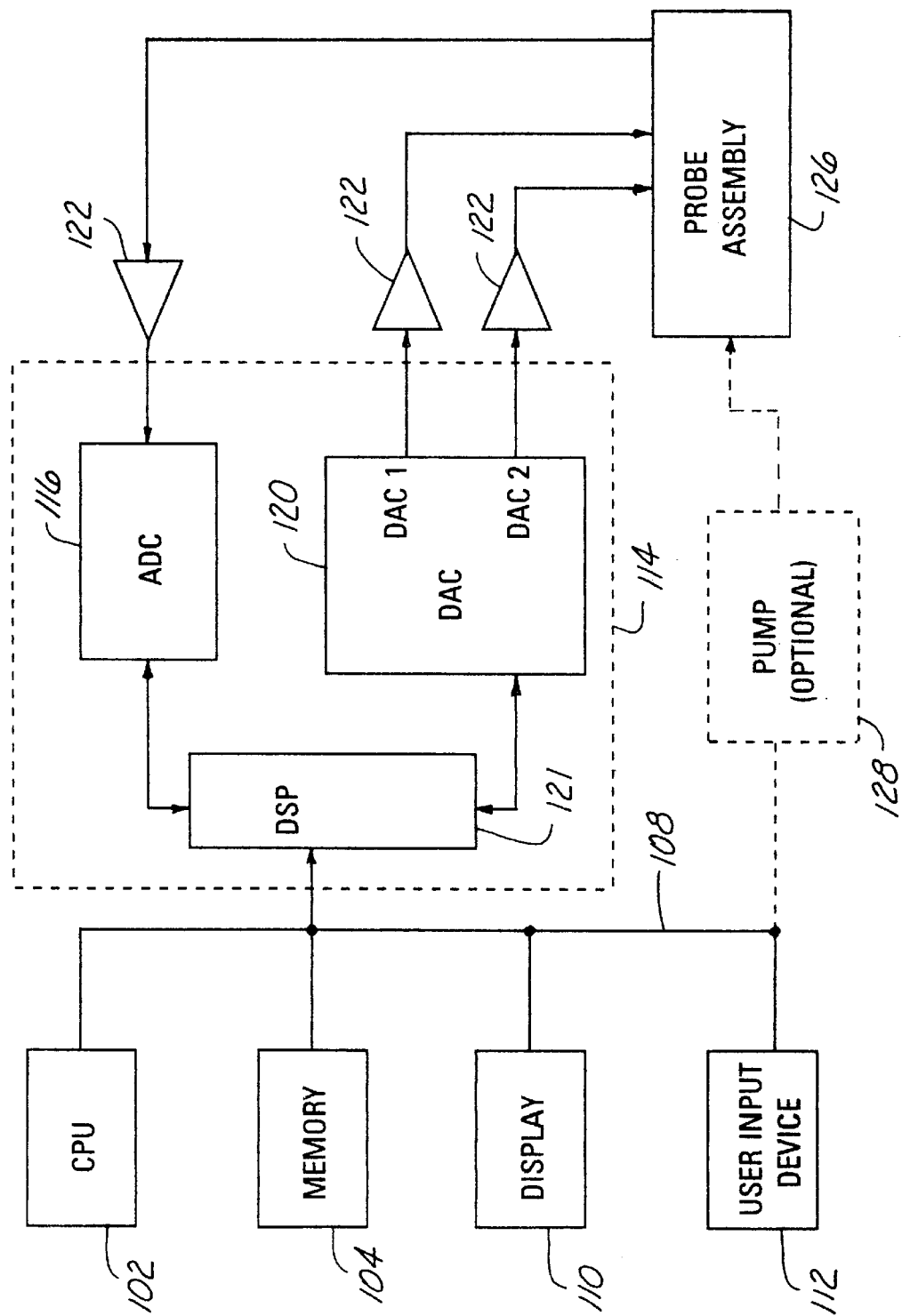
FIG. 1 is a functional block diagram of the system of the present invention.

The inventive system may be easily implemented on a conventional computer system. The present invention is embodied in a system 100 illustrated in the functional diagram of FIG. 1. The system 100 includes a CPU 102, which is a Pentium[1] CPU operating under MS-DOS[2]. A memory 104, which may include both random access memory (RAM) and read-only memory (ROM) is coupled to the CPU 102 by a bus 108. The bus 108 may carry power and control signals as well as data. A display 110 and user input device 112 are also coupled to the CPU 102 by the bus 108. The display 110 is a conventional video display and the user input device 112 may be a keyboard or a keyboard with cursor control device, such as a mouse, trackball, pen, or the like. The operation of these conventional components is well understood by those of ordinary skill in the art and need not be described herein. Other conventional components of the computer system, such as a disk drive, power supply, and the like are omitted here for the sake of brevity. However, it is understood that conventional computer components may also be used in the operation of the system 100. A hand-held, portable system (not shown) might also be constructed, with an appropriately installed CPU, data acquisition system, and probe assembly, which would serve to implement the inventive system. Data would be stored in temporary memory (not shown) and transferred to a remote computer system for further analysis.

[1] Pentium is a trade name of Intel Corporation.
[2] MS-DOS is a trade name of Microsoft Corporation.

The system 100 also includes an Ariel DSP32C data acquisition system 114, with Ariel Proport analog-to-digital converters (ADC) 116 and digital-to-analog converters (DAC) 120 and an AT&T digital signal processor (DSP) 121. The DSP 121 is used to digitally generate the stimuli described herein and to process signals received in response to the stimuli. In the presently preferred embodiment, the system 100 uses either one or two outputs, labeled DAC1 and DAC2, from the DAC 120. The system 100 also includes filters 122 to filter the inputs to the ADC 116 and the outputs from the DAC 120. The sample rate chosen for the data acquisition system 114 is 16 kilohertz (kHz), which is sufficient for EOAE measurements up to 8 kHz. The filters 122 are lowpass filters with an 8 kHz cutoff frequency.

Figure 2:
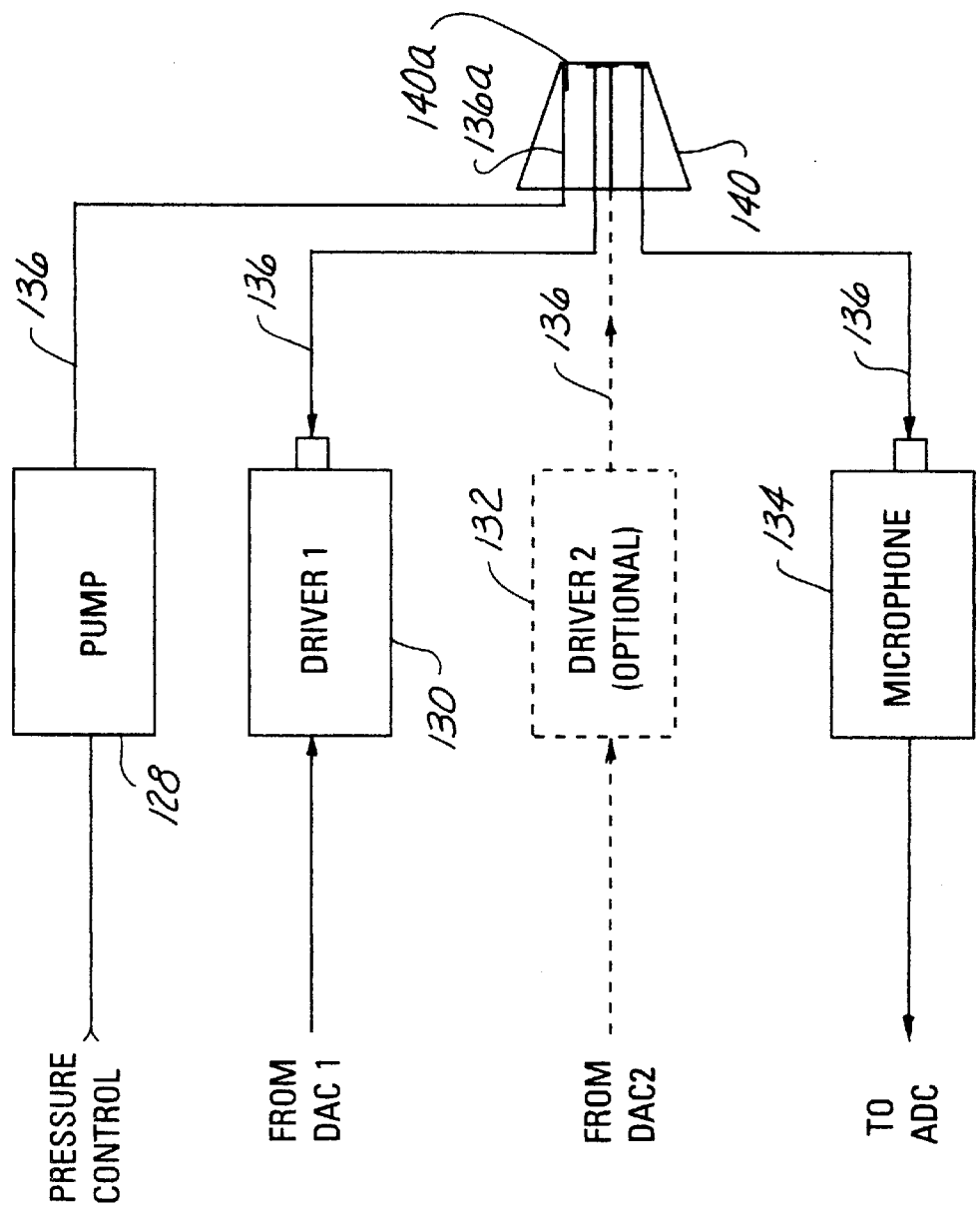
FIG. 2 is a functional block diagram of the probe assembly of the system of FIG. 1.

The data acquisition system 114 is coupled to a probe assembly 126, which is inserted into the subjects ear canal. Details of the probe assembly 126 are shown in the functional block diagram of FIG. 2. The probe assembly 126 includes an acoustic source 130, called Driver 1, which is coupled to the DAC1 output of the data acquisition system 114. In an alternative embodiment, the probe assembly 126 includes an optional second acoustic source 132, called Driver 2, which is coupled to the DAC2 output of the data acquisition system 114. The probe assembly 126 also includes a microphone transducer 134, which is coupled to the input of the ADC 116. The acoustic outputs of the drivers 130 and 132 and the acoustic input to the microphone 134 are each connected to an eartip 140 by an acoustic conductor 136, such as a flexible tube. The acoustic conductors 136 all terminate at a probe tip 140a of the probe assembly 140 that is inserted into the ear canal.

The probe assembly 126 may be a commercially available product such as the Etymotic ER-10C, which contains the microphone 134, Driver 1 as one acoustic source 130, and Driver 2 and the second acoustic source 132. In an alternative embodiment, the probe assembly 126 have contain only the microphone 134 and Driver 1 as the single acoustic source 130. Some preliminary results described herein were obtained using the single-source alternative embodiment, that is, the stimulus delivered to the acoustic source 130 using only the DAC 120 channel DAC1. The subject in all cases was an adult male with normal hearing. Responses were also obtained in a conventional one cubic centimeter (1-cc) coupler (not shown) to compare the noise floor and probe nonlinearities.

The CPU 102 includes an optional port to control the input to an optional static pressure pump 128 that is included in the system 100. The varying static pressure is coupled via an external probe tube 136 (see FIG. 2) to probe assembly 126, which includes an internal probe tube 136a to couple variations in static pressure to the ear canal.

The operation of the system 100 may now be described in detail. A new class of stimuli is defined as follows and synthesized on the CPU 102. The first step constructs an N-sample window with a deterministic waveform $s_1(t)$. Here, the time variable is denoted by t, but it is understood that in a discrete-time implementation that the waveform is defined at each of N discrete time steps. The second step constructs an N-sample window with the waveform $s_2(t)$. The third step constructs an N-sample window with the superposition of these two waveforms, $s_{12}(t)=s_1(t)+s_2(t)$. The composite stimulus s(t) is formed as a 3N-sample window whose initial N samples in the first window contain $s_1(t)$, whose intermediate N samples in the second window contain $s_2(t)$, and whose final N samples in the third window contain $s_{12}(t)$. Without loss of generality, the initial, intermediate and final windows may be permuted.

The response in the ear canal is measured to this 3N-sample stimulus s(t), and time-averaged in the preferred embodiment through multiple presentations of the stimulus. The response is partitioned into three N-sample windows, defined as the response $p_1(t)$ to the stimulus $s_1(t)$, the response $p_2(t)$ to the stimulus $s_2(t)$, and the response $p_{12}(t)$ to the stimulus $s_{12}(t)$.

The stimulus has the property that $$s_{12}(t)-s_1(t)-s_2(t)=0, \quad (1)$$

and the linear response of the ear or coupler is eliminated by forming the distortion pressure response $$p_D(t)=[p_{12}(t)-p_1(t)-p_2(t)]. \quad (2)$$

This is an extremely broad class of evoked responses that depend upon the specific choices of $s_1(t)$, $s_2(t)$ and $s_{12}(t)$. A desirable reduction in probe distortion is achieved by specific choices of $s_1(t)$ and $s_2(t)$, with $s_{12}(t)$ constrained in value by equation (1). One novel family of stimuli is that for which $s_2(t)$ is equal to $s_1(t)$, but delayed in time and scaled in amplitude, that is, $s_1(t)$ and $s_2(t)$ take the form $$s_1(t)=a(t), \quad (3)$$

$$s_2(t)=\epsilon a(t-\tau_m) \quad (4)$$

where the amplitude ratio $\epsilon$ has a positive or negative value and the relative time delay is $\tau_m$. The resulting response $p_D(t)$ to this family of stimuli is called the Double-Evoked Otoacoustic Emission (2EOAE). The waveform a(t) is an arbitrary N-sample array of values. The time delay is chosen to be within the range of the EOAE duration (<20 msec). The only constraint on a(t) is that the substantively non-zero response of both a(t) and $a(t-\tau_m)$ lie within the N-sample window of each. This means that the delay $\tau_m$ cannot be too large compared to the overall duration of the N-sample window. This is not a problem in practice, as $\tau_m$ ranges in values from 0–10 msec, with preferred embodiments in the 0–2 ms range, whereas the window duration is at least 20 msec. The stimulus $s_{12}(t)$ takes the form $$s_{12}(t)=s_1(t)+s_2(t)=a(t)+\epsilon a(t-\tau_m) \quad (5)$$

The signal a(t) is superposed with a delayed copy of itself (re-scaled in amplitude), such that the evoked OAE response to a(t) overlaps the evoked OAE response to $a(t-\tau_m)$ and the nonlinear interaction in the overlap region is controlled by the relative amplitude $\epsilon$. The novel aspect is the subtraction technique for the distortion response $p_D(t)$, which contains a nonlinearly evoked OAE that includes overlapping cochlear reflections to overlapping signals. As previously discussed, Kemp and Chum (1980) and Kemp (1986) described a double-click stimulus with overlapping responses, but the subtraction procedure of equation (2) was not used to obtain a response and time gating over the initial 6 msec of the lower-level click response was needed. The use of masker clicks of opposite polarities in this prior art may introduce probe distortion for peak overloading that is asymmetrical between positive and negative polarity clicks. The extent of the distortion increases with increasing click level and may be important for levels used in hearing screening. The stimuli in the Kemp and Chum (1980) double-click procedure do not sum to zero. In contrast, equation (2) is used without time gating with a procedure that controls for the probe distortion introduced individually by each source outputting a click. The distortion response $p_D(t)$ thus contains a nonlinearly evoked OAE that includes overlapping cochlear reflections to overlapping signals.

There remains arbitrariness in the choice of a(t). One interesting choice is where a(t) is a click (also termed a pulse), that is, a short-duration signal whose spectral bandwidth is broad. Short duration signifies that the signal duration is less than the impulse response of the acoustic source 130 in the probe assembly 126. This leads to the Double Click-Evoked Otoacoustic Emission (2CEOAE). The generation of the 2CEOAE stimulus is discussed in detail below.

Another interesting choice is where a(t) has a duration that is long compared to the impulse response of the acoustic source 130 in the probe assembly 126, and which is on the order of the duration of evoked OAE responses. That is, the N samples comprising a(t) correspond to a time interval in the range of 20–40 msec. Such stimuli may, without loss of generality, be expressed as a click waveform (i.e., a short-duration waveform) that is allpass filtered. The allpass filter varies the phase of the signal, which influences the temporal distribution of energy, but the spectrum of the filtered signal is precisely the same as the spectrum of the click. Two sub-classes of allpass filters result in chirp waveforms and maximum likelihood sequences, but other choices exist as well.

The preferred embodiment of long-duration signals is the chirp waveform, whose allpass filter group delay, defined below, increases or decreases uniformly with frequency. This class of chirp stimuli leads to the Double-Chirp Distortion Product (2ChDP). The generation of the 2ChDP stimulus is discussed in detail below. Alternative embodiments use allpass filters whose group delays vary in a more complicated manner with frequency, including a quasi-random variation of group delay with frequency.

The 3N-sample stimulus s(t) may be output only by the acoustic source 130 or by both acoustic sources 130 and 132, each driven by a signal generator. In the single-source embodiment, each of the N-sample sub-windows is output by the acoustic source 130. In the preferred embodiment that $s_2(t)$ is a time-delay, re-scaled copy of $s_1(t)$, this time delay between $s_1(t)$ and $s_2(t)$ in the jointly presented window $s_{12}(t)$ reduces the level of probe distortion due to peak overload. If the time delay $\tau_m$ is chosen sufficiently large, then the peak value of $s_{12}(t)$ may be constructed to be much closer to 100. This reduction in peak overload during the subtraction of responses to form the distortion pressure leads to a reduction of probe distortion. Examples are presented below.

In the double-source embodiment of the system 100, $s_1(t)$ is output by the acoustic source 130, and $s_2(t)$ is output by the acoustic source 132. In the presentation of $s_{12}(t)$, defined as the superposition of $s_1(t)$ and $s_2(t)$, $s_1(t)$ is again output by the acoustic source 130 and $s_2(t)$ is output by the acoustic source 132. Thus, each of the acoustic sources 130 and 132 outputs only one signal at one level, and the subtraction technique substantively eliminates the distortion of each source from the output distortion response. This is in contrast to the prior art of CEOAEs and tone-burst EOAEs, which use only a single source and which do not maintain constant level from that source.

Some obvious extensions to this general formalism may be noted. One is that static pressurization may be included as a variable. The EOAE is measured at various static pressures, which provides information on the cochlear signal in the presence of external modifications to the middle ear, via changes in pressurization.

Another is that the multi-stimulus construction and subtraction technique is not limited to the use of two elementary signals, but may be extended to three or more elementary signals. The above described a stimulus s(t) created by joining sub-stimuli $s_1(t)$, $s_2(t)$ and $S_{12}(t)$. Three or more time-delayed copies of a(t) may be used in the construction of these stimuli, the only constraint being that a linear combination of stimuli sum to zero. It is also possible to consider sequences combining $s_{123}(t)$, $s_{12}(t)$, $s_{23}(t)$, $s_{13}(t)$, $s_1(t)$, $s_2(t)$, and $s_3(t)$ in a manner that a linear combination of the stimuli sum to zero. Here, $s_{123}(t)$ denotes the superposition of $s_1(t)$, $s_2(t)$, and $s_3(t)$, etc. For this case of three sub-stimuli, there also exist single-source, double-source and triple-source variants that control more completely for probe distortion.

Double-Click-Evoked Otoacoustic Emissions

A short-duration signal $s_1(t)$ is defined by equation (3) above where a(t) is a short-duration, broadband waveform (click). A second short-duration signal $s_2(t)$ is defined by equation (4) above as a time-delayed version of $s_1(t)$ with amplitude scaled by $\epsilon$. The constant $\epsilon$ may take on arbitrary positive or negative values. A negative value inverts the polarity of the click. The composite signal $s_{12}(t)$ is defined by equation (5).

The acoustic pressure responses to the stimuli $s_1(t)$, $s_2(t)$ and $s_{12}(t)$ are $p_1(t)$, $p_2(t)$ and $p_{12}(t)$, respectively. The Double-Click-Evoked Otoacoustic Emission (2CEOAE) is defined by the response $$p_D(t) = p_{12}(t) - [p_1(t) + p_2(t)]. \qquad (6)$$

This equation is precisely equivalent to equation (2) for the case that $s_1$ is a click.

This is in contrast to the click-evoked OAE in which a stimulus s is presented at two amplitude levels, notated by $s(t, L_1)$ and $s(t, L_2)$, where $L_2 = L_1 + \Delta L$. The pressure responses at levels $L_1$ and $L_2$ are $p(t, L_2)$ and $p(t, L_1)$, and the click-evoked OAE is $$\Delta p = p(t, L_2) - p(t, L_1). \qquad (7)$$

The 2CEOAE of the system 100 manipulates the time delay $\tau_m$ between clicks as an independent variable, and there is no time-gating of the response with respect to the onset of the stimulus, as there is in prior-art, click-evoked OAE techniques. A further advantage is that any linear response of the system is canceled in calculating the 2CEOAE.

It is useful to calibrate the measurement system by applying the stimulus to the probe when inserted into a cylindrical tube. Any peak distortion in the probe can be measured and the spectral amplitude of the stimulus can be adjusted to eliminate the low-frequency energy that is predominantly responsible for overloading the source transducer.

The 2CEOAE measurement procedure has an advantage over the standard CEOAE measurement procedures (Kemp (1989)) since the level of the signal is not varied. Since the peak values associated with $s_1(t)$ are well-separated in time from the peak values associated with $s_2(t)$, then any probe nonlinearity will tend to be equivalent in the single-click and double-click conditions and will thus tend to cancel when equation (6) is used to calculate the 2CEOAE response. In contrast, the click-evoked OAE paradigm varies the level of the stimulus, so that any probe nonlinearity does not cancel when equation (7) is used to calculate the response. This is a critical difference for measuring evoked emissions with latencies less than 5 msec, i.e., high-frequency EOAES, and low-frequency emissions, which are significantly limited by probe distortion.

Sample waveforms for the 2CEOAE stimulus are illustrated in FIGS. 3A to 3C where different time delays $\tau_m$ are illustrated in each figure. It should be noted that FIGS. 3A to 3C and other Figures illustrate time varying waveforms. The amplitude of these waveforms is given in counts on the ADC 116 (see FIG. 1) and are thus displayed in arbitrary units. The time scale is given in terms of samples in the ADC 116. FIG. 3A illustrates the three signals, $s_1(t)$, $s_2(t)$, and $s_{12}(t)$ with a delay of $\tau_m = 1$ msec. FIGS. 3B and 3C have identical amplitudes, but time delays $\tau_m$ of 2 msec and 3 msec, respectively. The scaling factor is $\epsilon = 1$ in all three examples of FIGS. 3A to 3C. The waveforms in FIGS. 3A to 3C are taken directly from the output of the DAC1 (see FIG. 1). A variant of the 2CEOAE, using both DAC1 and DAC2, will be discussed below. There are 2048 samples in each composite waveform, corresponding in an overall duration of 128 msec for the sample rate of 16 kHz. Consider the 3 msec time delay stimulus of FIG. 3C. The first third of the waveform in FIG. 3C is $s_1(t)$ with a duration of 682 samples, the middle third of the waveform in FIG. 3C is $s_2(t)$ with the same duration of 682 samples, and the last third of the waveform in FIG. 3C is $s_{12}(t)$ (i.e., $s_{12}(t) = s_1(t) + s_2(t)$) with a duration of 682 samples, terminated by two additional samples with a zero value. These latter two samples are present in these pilot data and their influence is negligible, but the preferred embodiment has the duration of each of the three sub-windows precisely identical. After the subtraction processes in equation (6) are carried out, the 2CEOAE responses have a duration of D=43 msec, and the CEOAE response has a duration of 32 msec.

The 2CEOAE stimulus illustrated in FIGS. 3A to 3C are contrasted with the conventional linearly balanced set of stimuli illustrated in FIG. 4 and discussed in Kemp (1989). In FIG. 4, each of the stimuli in the set are separated in time so that only one click occurs within the maximum latency for the evoked response from the ear. As discussed above, the time interval between stimuli in Kemp (1989) is at least 20 msec. As such, the stimulus in FIG. 4 comprises four separate stimuli that each have a corresponding evoked OAE response from the ear. In contrast, the 3N sample stimulus s(t) generated by the system 100, and illustrated in FIGS. 3A to 3C, have three independent stimuli, but the third stimulus includes two clicks presented with the time delay $\tau_m$ that is less than the maximum latency time for the evoked response from the ear. It should be noted that the 3N sample stimulus may be presented in any order.

2CEOAE Variants

There are two variants of the measurement procedure, using only the acoustic source 130 (see FIG. 3) or both of the acoustic sources 130 and 132. A single acoustic source can be used with sufficiently large time delay $\tau_m$, because the response to the joint presentation of $s_1(t)$ and $S_2(t)$, followed by subtraction of each of the single responses to $s_1(t)$ and $s_2(t)$, produces negligible distortion artifact. The presence of delay offsets the peak values associated with $s_1$ and $s_2$, thereby making the subtraction process effective. In the case of zero delay, the two clicks coalesce into a single acoustic click of twice the amplitude, thereby producing much greater amounts of peak clipping in the single acoustic source. This undesirable property is similar to the technique of Kemp (1989), who substracts responses based upon clicks of different amplitudes. The variant in which $s_1(t)$ is input to the acoustic source 130 and $s_2(t)$ is input to acoustic source 132 totally eliminates peak clipping distortion. This is the preferred embodiment, although at slightly increased complexity and cost for the probe assembly 126 (see FIG. 2).

This double-source variant has a surprising, and significant, degenerate case, when the time delay between the clicks is zero ($\tau_m = 0$), and when the relative click amplitude is unity ($\epsilon = 1$). The two click stimuli again coalesce into a single click of twice the amplitude, assuming, without loss of generality, that the two acoustic sources 130 and 132 are identical. By the use of separate acoustic sources 130 and 132 for $s_1(t)$ and $s_2(t)$, the differential subtraction embodied in equation (6) absolutely eliminates probe nonlinearity that is synchronous to the stimulus window. This allows measurement of a CEOAE without the need for nulling out (i.e., time-gating) the initial 2–5 msec of the response, and allows for much wider bandwidth measurements of CEOAEs. This technique is not obvious, having been constructed by the intermediate interpretation of CEOAEs as a form of double-evoked otoacoustic emission.

Double-Chirp Distortion Product Stimulus

The operation of the system 100 may now be described in detail for the case of a double-chirp stimulus, resulting in the double-chirp-evoked distortion product (2ChDP). The double chirped stimulus signal is synthesized by the system 100 and delivered to the ear. The double chirp stimulus has significant advantages over both the conventional two frequency DP stimulus and the conventional click stimulus. Conventional distortion product systems use a pair of sinusoidal signals with frequencies $f_1$ and $f_2 > f_1$ to evoke distortion products at frequencies including $2f_1 - f_2$ and other frequencies that are linear combinations of the two stimulus frequencies.

Such conventional DP systems have the advantage that the strongly evoked signals are widely separated in frequency from those in the stimulus, so that they can easily be extracted. They have the disadvantage that the response is obtained at only a single pair of stimulus frequencies, which must be varied to obtain a broad bandwidth response. Typically, special frequencies are used for $f_1$ and $f_2$ whose periods are exact subharmonics of the number of the samples N in the window. Such limitations of frequency simplify the digital generation of the stimuli. For example, a 1000-sample window may be used to continuously generate a sine wave whose period is 1000 samples, 500 samples, 250 samples, or any other period that is an exact sub-harmonic of the window period. While this simplifies the synthesis of stimuli, it severely constrains frequency selectivity. This problem is compounded by the property that the DP response may fluctuate significantly if the stimulus frequencies are co-varied by small amounts, for example, in the vicinity of a SOAE site. This means it would be desirable to have a broader range of frequency selectivity in DP measurements. This is made possible with 2ChDP measurements.

Click-evoked OAE measurement system have good frequency selectivity, but the linear response overlaps somewhat in time from the nonlinear response, and, even with appropriate time-domain averaging, there may be limitations in the bandwidth of the evoked OAE response that can be measured when compared to DP systems.

Techniques using chirp-based distortion products by the system 100 share advantages with both DP and click-evoked OAE measurement systems. The double chirp stimulus uses a repetitive, but non-continuous, signal well-suited to time-averaging. Compared to a short-duration pulse, a chirp has a greater signal-to-noise ratio and a reduced crest factor, thereby reducing nonlinearities in the acoustic source 130. The crest factor is the ratio of the peak to RMS amplitude of the signal.

A wideband multi-chirp stimulus can be created with controllable crest factor whose strongly-evoked cochlear response components are separable from those of the stimulus. Furthermore, such a stimulus has desirable group delay properties for DP measurements. This is achieved using a double chirp, that is, designing a stimulus that is a linear superposition of two chirps. The 3N sample stimulus is defined by equations (3) to (5) above. The signal $s_1(t)$ is defined by equation (3) where a(t) is a chirp signal. The signal $s_2(t)$ is defined by equation (4) above as a time-delayed version of $s_1(t)$ with amplitude scaled by $\epsilon$. The composite signal $s_{12}(t)$, defined by equation (5), is the superposition of $s_1(t)$ and $s_2(t)$. However, as previously discussed, the system 100 is not limited to stimuli $s_1(t)$ and $s_2(t)$ that are scaled replicas of each other. The 2ChDP EOAE is defined by equation (6).

Linear and Log Chirp Design

Figure 5:
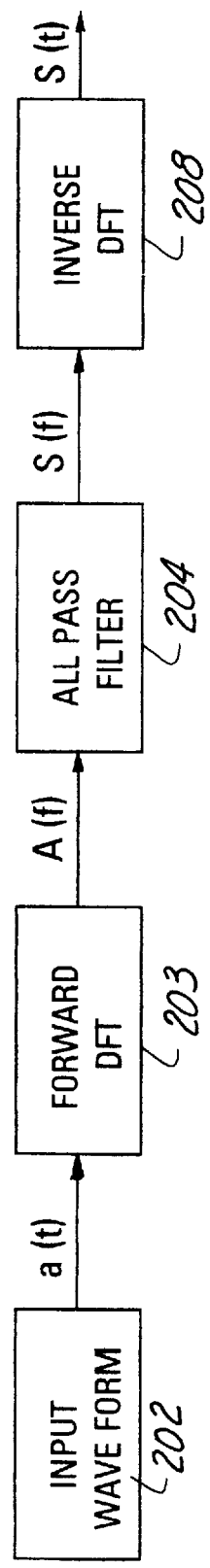
FIG. 5 is a functional block diagram of a chirping circuit of the system of FIG. 1.

The design procedures for producing chirps with linear and logarithmic group delay are summarized in this section. As is known in the art of signal processing, a chirp signal is generated by filtering a click with an allpass, or phase shift, filter. This is illustrated in the functional block diagram of FIG. 5 where a chirping circuit 200 includes an input waveform 202 representing the signal a(t). The signal a(t) is processed by a discrete Fourier transform (DFT) 203 to convert the signal a(t) into a frequency domain signal A(f). An allpass filter 204 processes the frequency domain signal A(f) to produce a chirp whose spectrum contains the same energy as the original signal a(t), but whose energy is spread out in time due to the phase shifting. The present description uses upper-case letters to denote frequency-domain variables, and lower-case letters to denote time-domain variables. As will be described in detail below, the allpass filter 204 can have a linear dependence on frequency to produce a linear chirp or a logarithmic dependence on frequency to produce a log chirp.

Since the 2ChDP is a particular embodiment of the 2EOAE stimulus design, the initial signal a(t) may be specified in the time domain or using its DFT 203, A(f), may be specified in the frequency domain. The preferred embodiment of a(t) is a short-duration signal similar to a click. This short-duration signal is filtered by the allpass filter 204, and transformed to a time-domain signal using an inverse discrete Fourier transform (DFT$^{-1}$) 208. The chirped signal is essentially a time-stretched band limited impulse. The chirping circuit 200 is intended merely to illustrate the processing steps that are performed by the system 100 to generated the time-stretched band limited impulse.

The allpass filter 204 is expressed in the frequency domain by $C(f) = \exp\{j\Theta\}$ where the phase response $f$ varies with frequency $f$ or, equivalently, radian frequency $\omega = 2\pi f$, and where the unit imaginary number is j based upon a time dependence exp j$\omega$t. The function "exp" is the complex exponential function. The group delay $\Gamma$ of the allpass filter is defined by $$\tau = -\frac{1}{2\pi} \frac{d\Theta}{df} \qquad (8)$$

In a discrete-time implementation based upon a duration of N samples at a sample period of T, the group delay must be in the range of 0-D, where the window duration is D=NT. The k-th discrete frequency is $f_k = k/D$, where k varies from 0 ... (N−1). Suppose the upper frequency desired in the stimulus is $f_u$, which is less than $(2T)^{-1}$. The allpass filter 204 of the linear chirp is expressed by $$\Theta = -\beta \frac{f_k^2}{2f_u} D, \qquad (9)$$

$$\tau = \beta \frac{f_k}{f_u} D,$$

As $\beta$ varies from 0 up to 1 (or, 0 to −1), the corresponding maximum group delay varies from 0 to the window duration D, and the crest factor is uniformly decreased. For positive $\beta$, the group delay of the linear chirp linearly increases with increasing frequency. For negative $\beta$ the relationship is reversed.

The stimulus S(f) is specified as the product of the linear chirp allpass filter 204 with an amplitude response A(f) that is a real, non-negative quantity, and is constrained to be zero for frequencies above $(2T)^{-1}$. More generally, it is useful to specify A(f) such that it is non-zero only within the passband of the acoustic source 130 (see FIG. 2), and it can be further varied with frequency to optimize the signal-to-noise ratio, the crest factor of the stimulus or measured response, or other desired quantity. The inverse DFT (DFT$^{-1}$) of $S(f)=A(f)C(f)$ is the chirp waveform s(t) used as $s_1(t)$ in a double-chirp stimulus presentation.

The log chirp is constructed using the allpass filter 204 whose parameters are selected so that the group delay is proportional to the logarithm of the frequency. Its phase function $\Theta$ may be expressed as $$\Theta = 2\pi\alpha D f_k \left[ \log\left(\frac{f_k}{f_c}\right) - 1 \right]. \tag{10}$$

The center frequency $f_c$ is the geometrical mean of the lowest ($f_l$) and highest frequencies present, $f_c=\sqrt{f_l f_u}$. The log function is the common log (base 10). The group delay is calculated to be $$\tau = -\alpha D \log\left(\frac{f_k}{f_c}\right), \tag{11}$$

thus verifying that the group delay varies logarithmically with frequency. When $\alpha$ is positive, the group delay at high frequencies is less than that at low frequencies; when $\alpha$ is negative, these relationships are reversed. The group delay equals zero at the center frequency.

The chirp amplitude $A(f)$ must be of finite bandwidth and avoid the logarithmic singularity at zero frequency. There is a low-frequency transition regime (just above $f_l$) in which the chirp amplitude is increased from zero to unity gain. There is a high-frequency transition regime (just below $f_u$) in which the chirp amplitude is decreased from unity gain down to zero. The chirp amplitude $A(f)$ may otherwise be smoothly varied within the passband, as desired.

$$T_g = |\alpha| D \log\left(\frac{f_u}{f_l}\right). \tag{12}$$

Since the number of octaves in the passband is $N_{oct}=\log_2(f_u/f_l)$, it follows that $$T_g = 0.301|\alpha|DN_{oct}, \tag{13}$$

which implies that $|\alpha|$ should be less than $(0.301N_{oct})^{-1}$ so that $T_g$ is less than D. In practice, the log chirp has a shorter duration than this limit so that the EOAE response is contained within the sampling window.

After the inverse DFT, the log chirp can be arbitrarily rotated within the buffer of N samples to align its onset near the beginning of the buffer, thus translating the absolute zero of the center-frequency group delay to any convenient value.

Double-Chirp Distortion Product Measurement

The system 100 allows the delivery of two chirp signals to the ear to elicit a 2ChDP emission from the cochlea. In this embodiment, either one acoustic source 130 or two acoustic sources 130 and 132 are used to generate the respective chirp signals, as discussed above in the single-source and double-source embodiments of the general 2EOAE measurement. The 2ChDP stimulus offers the dual benefits of broad frequency response not available with the conventional DPOAE technique and good control over probe nonlinearities. The basic idea is to present two log chirps, $s_1(t)$ and $s_2(t)$, with a well-defined relationship between group delay and level. The log chirp is selected in the presently preferred embodiment because it is well known that the tonotopic organization of the cochlea is logarithmic in frequency. Nevertheless, the system 100 is intended to encompass the linear chirp stimulus as well as other chirp designs and other allpass filters, as discussed above in the general case of the 2EOAE measurement. Intuitively, each log chirp resembles, over extremely short time scales, a swept sine wave. If two sine waves are swept simultaneously, such that their frequency ratio $m=f_2/f_1>1$ is maintained constant, then a swept DP response will be evoked. In the presently preferred embodiment, three stimuli are used, $s_1(t)$, $s_2(t)$, and their superposition, $s_{12}(t)=s_1(t)+s_2(t)$, and the three corresponding ear-canal pressure responses $p_1(t)$, $p_2(t)$ and $p_{12}(t)$, respectively, are measured. The linear component of the pressure response is subtracted out using equation (6) above. As in the general case of 2EOAE measurements, the corresponding superposition of stimuli, $s_{12}(t)-(s_1(t)+s_2(t))$ in the 2ChDP stimulus, is identically equal to zero. The response $p_D(t)$ is the 2ChDP. It is the nonlinear signal that remains from the joint presentation of two chirps, after subtracting out the individual responses to each chirp. While $p_1(t)$ and $p_2(t)$ may themselves be level-dependent, each invoking an EOAE, their joint presentation produces DP components.

In contrast to the conventional DP measured with a pair of sine tones, the 2ChDP is defined at all frequencies in the measurement bandwidth. In standard usage, the amplitude spectrum of chirp $S_1(f)$ is $A_1(f)=A(f)$, and that for chirp $S_2(f)$ is $A_2(f)=\epsilon(f) A(f)$ where $\epsilon$ is the scaling factor. The sub-class of stimuli with constant $\epsilon$ has interesting properties. A positive value of $\epsilon$ makes the polarity of $s_2(t)$ the same as $s_1(t)$, whereas a negative value of $\epsilon$ produces stimuli with opposite polarity. The chirps differ in level by $\Delta L=20\log|\epsilon|$. This enables the amplitude spectrum of the overall signal to be adjusted as desired, but a well-defined spectral level difference is produced that is constant across frequency. This is typical in common DP measurement paradigms.

How does one further emulate DP measurement paradigms, in which a fixed ratio $m=f_2/f_1$ is maintained between the stimulus frequencies, while $f_1$ is varied? The solution is that the group delay $\tau_1$ of chirp $s_1(t)$ at frequency $f_1$ should be equal to the group delay $\tau_2$ of chirp $s_2(t)$ at frequency $f_2$. It follows that these group delays take the form $$\tau_1(f) = -\alpha D \log\left(\frac{mf}{f_c}\right), \tag{14}$$

$$\tau_2(f) = -\alpha D \log\left(\frac{f}{f_c}\right),$$

where the discrete index k of the frequency bin has been suppressed.

The corresponding allpass phase functions, $\Theta_1$ and $\Theta_2$, are needed to construct the stimuli $s_1(t)$ and $s_2(t)$, respectively, and are calculated from $$\Theta_1(f) = 2\pi\alpha Df \left[ \log\left(\frac{mf}{f_c}\right) - 1 \right], \tag{15}$$

$$\Theta_2(f) = 2\pi\alpha Df \left[ \log\left(\frac{f}{f_c}\right) - 1 \right].$$

Thus, the signal $S_1(f)=A_1(f)e^{j\Theta_1}$, and the signal $S_2(f)=A_2(f)e^{j\Theta_2}$.

While the correspondence of the 2ChDP with the DP measurement paradigm has been stressed, it is also interesting to contrast its properties with other forms of EOAE responses. Evoked-OAE responses typically rely on the subtracted response to a stimulus presented at different levels, whereas the 2ChDP response is a subtracted response to a set of stimuli whose levels are maintained. It has been argued that DPOAE measurements have better signal-to-noise properties than CEOAE measurements because DPOAE responses do not rely on subtracting out the signal response at different levels. The 2ChDP measurement of the system 100 shares this desirable property with DPOAE systems.

Figure 6A:
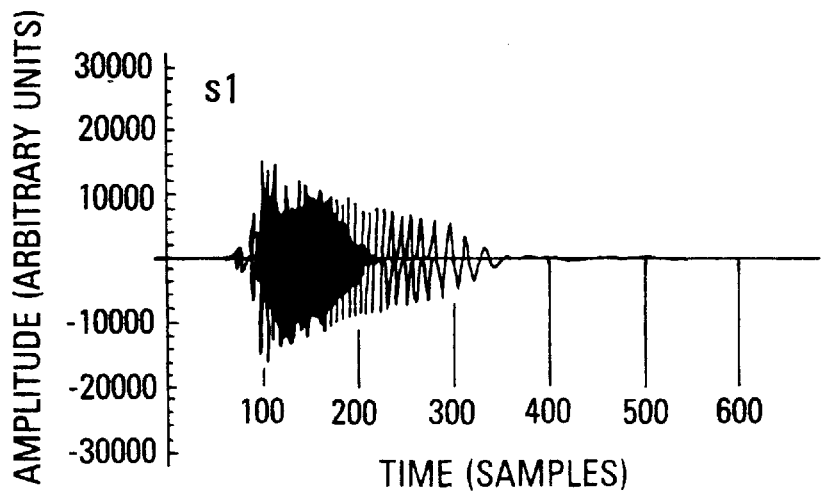
FIGS. 6A to 6C are waveforms illustrating the chirped stimuli generated by the chirping circuit of FIG. 5.
Figure 6B:
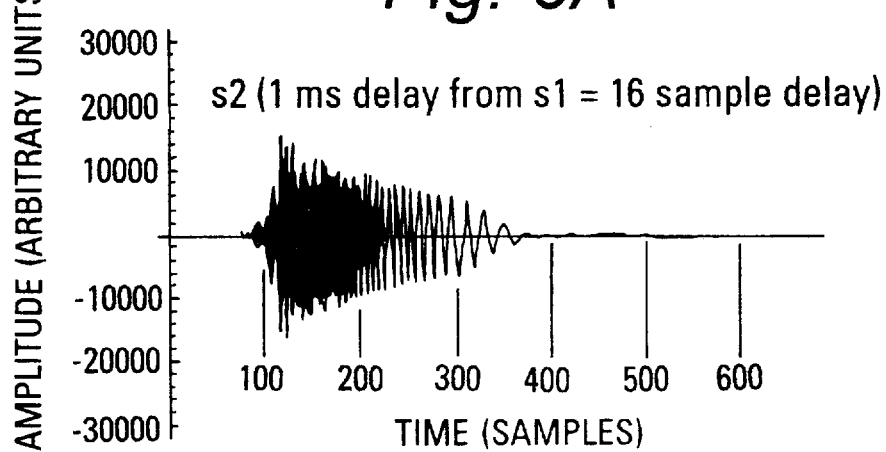
Figure 6C:
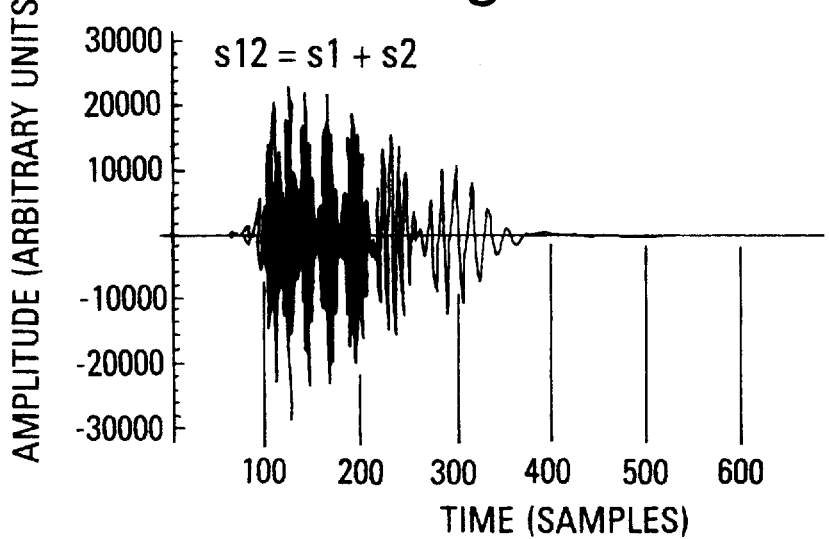

An example of a log chirp stimulus set is illustrated in FIGS. 6A to 6C. The amplitude spectrum A($f$) was constant from 500–7800 Hz, with a smooth, half-Hamming window in the spectral domain at frequencies below 500 and above 7800 Hz. The high-frequency roll-off prevented any aliasing difficulties, although both the ADC 115 and DAC 120 have excellent anti-aliasing filters 122. This Hamming window in the frequency domain leads to smooth onset and decay properties in the time-domain waveform. The relative amplitude was set to unity ($\epsilon=1$), and the log chirp coefficient was $\alpha=0.15$. A time delay $\tau_m=1$ msec was created for $s_2(t)$ relative to $s_1(t)$. Although the peak amplitudes are only slightly less than those of corresponding click waveforms, there is much more energy in the chirp waveforms because the energy is spread out temporally.

FIG. 6A illustrates the first chirp waveform $s_1(t)$ generated at the output of the DAC 1. FIG. 6B illustrates the second chirp waveform $s_2(t)$ generated at the output of the DAC 1. As discussed above, a 1 msec time delay was selected for $s_2(t)$ relative to $s_1(t)$. FIG. 6C illustrates the combination chirp waveform $s_{12}(t)$ generated at the output of the DAC 1. Some amplitude modulation effects are visible in the $s_{12}(t)$ waveform. The individual chirp waveforms $s_1(t)$ and $s_2(t)$ can be generated by only by the DAC1 coupled to the acoustic source 130 (see FIG. 2) or generated using both acoustic sources 130 and 132 with the chirp waveform $s_1(t)$ being generated by the DAC1 coupled to the acoustic source 130 while the chirp waveform $s_2(t)$ is generated by the DAC2 coupled to the acoustic source 132. In this latter embodiment, the combination chirp waveform $s_{12}(t)$ is generated acoustically as a result of the independently generated outputs of the acoustic source 130 and the acoustic source 132.

It will be appreciated by those skilled in the art that the 2ChDP response defined in equation (6) differs from the frequency specific response in ordinary DP measurements. When the magnitude of the 2ChDP response is converted to sound pressure level (SPL), so removing the phase information, the response is similar to that of a broadband CEOAE measurement. It is the phase information that enables the tracking of frequency-specific distortion products such as $2f_1-f_2$. Each of these frequencies is swept in the chirp stimulus, so that each distortion product is swept in the 2ChDP response. The phase of the signal can be used for time to construct individual trajectories of distortion-product components over time. Useful techniques for calculating such trajectories include wavelet analysis or time-frequency analysis. The latter is the preferred class of embodiment, and the particular time-frequency analysis technique is the Choi-Williams transform. Since the 2ChDP response is broadband, it becomes possible to calculate each distortion product trajectory, whose frequency is $mf_1+nf_2$ for integers m and n, with significant spectral energy. It is in this way that an equivalence in the representations of double click-evoked and distortion product-evoked responses is constructed. The latency of each trajectory is influenced not only by the group delay of the allpass filter, but also by the frequency-specific latency of the otoacoustic emission, involving travel-time to the cochlear reflection site (or sites), and back.

2ChDP Variants

The 2ChDP procedure offers significant advantages over existing systems. The set of stimuli may be output by the single acoustic source 130 (see FIG. 2), and probe nonlinearity is partially controlled for by the subtraction process of equation (6). This variant is similar to the linear cancellation procedures used in CEOAE systems, but may be superior due to the lower crest factor of the chirp stimulus. As described below, there is no need to null out the beginning of the 2ChDP response for a certain range of m. Thus, the system 100 offers an advantage over conventional systems in that the short latency response can provide useful information about high frequency EOAE.

The second, and preferred embodiment if the additional cost of the probe assembly 126 is not a problem, is to use the two acoustic sources 130 and 132. The first acoustic source 130 outputs the first stimulus $s_1$ and the second acoustic source 132 outputs the second stimulus $s_2$. This controls at all values of m for intermodulation distortion created by joint presentation of both stimuli using only the single acoustic source 130. This variant is similar to some DPOAE measurement systems that implement two separate acoustic sources, but has the additional advantage of wideband response, as discussed above.

The degenerate case is where m=0 and $\epsilon$ may be varied. When the two acoustic sources 130 and 132 are used, this degenerate case outputs the same frequency sine tone to each of the acoustic sources, and the response is a very precise measurement of the SEOAE without the need to assume that the OAE saturates. This is similar to the pulsed SEOAE and DPOAE method discussed in Observations on Simultaneous SFOAE and DPOAE Generation and Suppression, by D. T. Kemp et al., in *Mechanics and Biophysics of Hearing*, P. Dallos, C. Geisler, J. Matthews, M. Ruggiero, and C. Steele, editors, pages 202–209, Berlin, 1990, Springer-Verlag. However, the 2ChDP chirp stimulus is significantly different in that it provides a wideband measurements, whereas Kemp et al. use a pulsed sine tone of frequency $f_2$ on a background continuous tone of frequency $f_1$. The SEOAE measurement is when $f_2=f_1$.

The Dechirped 2ChDP Response

Figure 7:
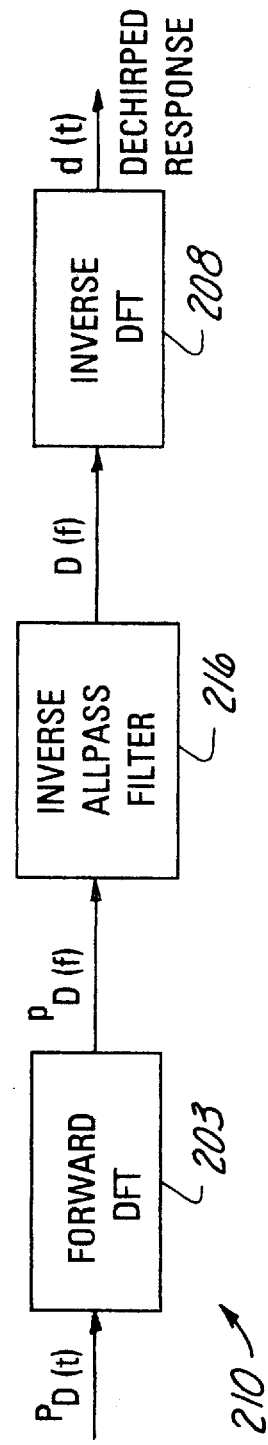
FIG. 7 is a functional block diagram of a dechirping circuit to dechirp the response evoked by the allpass filtered signal of FIG. 5.

The response $P_D(t)$ of equation (6) cannot be easily interpreted because the stimuli have been filtered by the allpass filter 204 (see FIG. 5), and the responses share this characteristic. One solution is to remove the influence of the allpass filter 204 using the dechirping circuit 210, shown in FIG. 7. The dechirping circuit 210 includes the forward DFT 203 to convert the response $p_D(t)$ from the time domain to the frequency domain. The dechirping circuit 210 then processes the frequency domain response signal by applying an inverse allpass filter 216 with the characteristic exp -j$\Theta$ to the frequency domain response. The inverse DFT 208 converts the output of the inverse allpass filter 216 from a frequency domain response to a time domain response. This time domain response is denoted as the dechirped response, since it represents the response to an equivalent click stimulus.

This operation is analyzed for the example of the log chirp stimuli. The log chirp stimuli are transformed using the forward DFT 214 to the frequency domain with transforms denoted by $S_1(f)$ and $S_2(f)$. Suppose the inverse allpass filter exp j$\Theta$ 216 is chosen. Equation (15) above implies the following simple relationship between the group delays and the phase functions (a similar relationship can be readily obtained for the linear chirp):

$$\tau_2(f)=\tau_1(f)+\tau_m,$$

$$\Theta_2(f)=\Theta_1(f)-2\pi f\tau_m, \qquad (16)$$

$\tau_m = \alpha D \log m$.

Double-chirp stimuli were constructed with time delays $\tau_m$ of 1, 2 and 3 msec. Using equation (16) above, the corresponding DP frequency ratios were m=1.4, 2.0 and 2.9, respectively. The 1 msec delay case is most closely related to frequency ratios used in typical DP experiments. There is no limitation in using even smaller time delays to produce DP frequency ratios between 1.0–1.4.

It follows that the dechirped responses $D_1$ and $D_2$, respectively, are $$D_1(f) = e^{-j\Theta_1} S_1(f) = A(f),$$

$$D_2(f) = e^{-j\Theta_1} S_2(f) = \epsilon A(f) e^{-2j\pi f \tau_m}. \quad (17)$$

Denoting the impulse response of the filter $A(f)$ by $a(t)$, the dechirped time-domain stimuli are $$d_1(t) = a(t),$$

$$d_2(t) = \epsilon a(t - \tau_m), \quad (18)$$

where $d_i(t)$ is the inverse DFT of $D_i(f)$ for i=1 or 2. The form of the latter equation is due to the time-shift properties of the DFT, as will be appreciated by those skilled in the art. The dechirped stimulus $d_{12}$ of the composite stimulus $s_{12}(t)$ is $$d_{12}(g) = \alpha(t) + \epsilon a(t - \tau_m). \quad (19)$$

If $\epsilon(f)$ varies with frequency, then the second term in the above is the convolution of $\epsilon(t)$ with $a(t-\tau_m)$.

An important conclusion is that the dechirped, double-chirp stimuli in the time domain is isomorphic to a pair of two short-duration pulses that vary in relative latency and level. This time-domain representation of the 2ChDP response allows data analysis within the framework of a response evoked by a pair of equivalent clicks. The form of equation (19) is equivalent to the general 2EOAE form of equation (5), as expected.

This exemplifies the novel relationship between DP measurements and evoked OAE measurements that differs in form from previous discussions comparing DPs and click-evoked OAEs. The dual to the frequency-domain DP response is the time-domain double-click response. DP measurements use a stimulus composed of two sine tones, and the parallel in the time domain uses two clicks.

Discussion

A feature of the 2CEOAE response that is not shared by the click-evoked response, is that the 2CEOAE response may be chirped to define an equivalent distortion-product response. The argument is precisely the inverse of that given earlier. The 2CEOAE responses are forward transformed using the DFT, allpass filtered using $\exp j\Theta_1$, and then plotted versus the group delay $\tau_1$. Alternatively, the phase reference of $\Theta_2$ may be adopted. Time-frequency representations and wavelet transformations may also be used to identify the equivalent DP trajectories in a two-dimensional time-frequency space. This introduces a new way to link understanding of distortion-product and click-evoked OAEs.

While the stimuli in the 2ChDP and 2CEOAE have a dual relationship between the chirped and dechirped conditions, their nonlinear responses may not be simply related. By comparing both 2ChDP and 2CEOAE responses under both conditions, the nature of the nonlinearity can be probed as regards its spectral and temporal distortion.

The magnitude of the 2CEOAE response may differ from that of the standard CEOAE due to the different normalizations in the subtraction procedures. Nevertheless, it is not the absolute magnitudes of the EOAE pressure responses that matter, but rather it is the magnitude differences between the EOAE and probe distortion, and the EOAE and the noise floor, that are important for setting detection thresholds in clinical applications of hearing screening and hearing diagnosis systems.

Both the 2ChDP and 2CEOAE methods have signal processing advantages over existing DP and evoked OAE methods that may lead to clinical applications, in particular, improved detection and diagnosis of cochlear impairments in neonatal and adult humans. These advantages may be enhanced with the power-weighted spectral amplitude algorithm proposed in the next section. In addition, the measurement of conductance and other components of impedance and reflectance would enable detection of conductive impairments, so that a combined system might be useful for simultaneous detection and diagnosis of both conductive and cochlear hearing impairments.

Acoustic Power Considerations

DP measurements have typically been reported in terms of constant SPL in the ear canal versus frequency, and OAE measurements have been reported in terms of constant peak SPL. Such pressure-based measures are influenced by the presence of standing waves in the ear-canal, individual differences, developmental factors in the age range from neonates to adults, middle-ear differences between senile and younger adults, and the presence of conductive impairments. For example, because the middle ear is inefficient at low frequencies, a large ear-canal pressure corresponds to a small power transfer. Because the middle is extremely efficient near 4 kHz, a small ear-canal pressure corresponds to a large power transfer. Such effects can be controlled at the level of input to the middle ear, by switching from a pressure-based measure to a power-based measure.

Two power-based measures have been proposed, reflectance and conductance. The energy reflectance is the ratio of reflected power to incident power in an acoustic plane wave impinging on the ear canal from a semi-infinite cylindrical tube. While immensely useful in characterizing the ear-canal response, the reflectance is not directly useful for measurements of acoustic power for experiments using probe assemblies in the ear canal. The conductance G is proportional to the power per unit squared pressure using an insert probe. That is, it directly maps SPL into absorbed power level, as discussed by Keefe et al., "Ear-Canal Impedance and Reflection Coefficient in Human Infants and Adults," J. Acoust. Soc. Am. 94:2617–2638, 1993. The power $\Pi(f)$ is expressed in terms of the conductance and measured pressure $P(f)$ by $$\Pi(f) = \frac{1}{2} G|P|^2. \quad (20)$$

The amplitude spectrum $A(f)$ of the stimulus can be weighted within the passband of the acoustic source 130 (see FIG. 2) by the power transferred to the middle ear. Suppose that the equivalent circuit parameters of the measurement system are well known, so that the overall transfer function $T(f)$ between the electrical stimulus $S(f)$ and the acoustic pressure $P(f)$ are known. It follows that a spectral amplitude $A(f)$ in the stimulus produces an pressure amplitude $|P(f)| = |T(f)| A(f)$.

The conductance $G(f)$ is measured at the entryway of the probe assembly 126 within the ear canal. Without changing the position of the probe assembly 126, the power Π absorbed by the ear is $$\Pi(f) = \frac{1}{2} G|T|^2 |A|^2, \quad (21)$$

so that the power in the stimulus passband is maintained at a constant magnitude $\Pi_0$ with the choice $$A(f) = \sqrt{\frac{2\Pi_0}{G|T|^2}}. \quad (22)$$

Except for variations in the transducer transfer function, the spectral amplitude in the stimulus is weighted by $1/\sqrt{G(f)}$. Such a weighting in adults tends to diminish the spectral level near 4 kHz and enhance it near 1 and 8 kHz, which is precisely where DP components are more difficult to measure. In addition, power-based spectral weightings are relevant for studies of human development, because the conductance varies with age for human infants in the range of 0–24 months, as compared to adults.

The boost in the low-frequency stimulus energy is limited by probe distortion, since low-frequency components are influential in producing high peak levels. Thus, the power-based approach must be balanced by the presence of probe distortion. An alternative embodiment in the 2ChDP stimulus design is to use the allpass filter 204 (see FIG. 5) that is not strictly logarithmic in frequency (a log chirp is already preferable to a linear chirp in this respect), so that the low frequency energy is spread out over a broader range of delay times.

Implementation

The implementation issues are common for the 2ChDP and 2CEOAE procedures. Each stimulus and response is based upon an N-sample window with duration D. A 3N-sample sequence is defined by $s_1(t)$, $s_2(t)$, $s_{12}(t)$. To allow time-averaging of responses and ensemble averaging of spectral coherence, each sequence is repeated 2E times to form an ensemble of two sub-ensembles, each sub-ensemble having a length of E sequences. Numbering each sequence in the ensemble from 1, . . . , 2E, sub-ensemble A contains sequences 1, 3, . . . , 2E–1, and sub-ensemble B contains sequences 2, 4, . . . , 2E. Thus, the sequences are interleaved within each sub-ensemble. A typical value for the size of each sub-ensemble is E=8, and the ensemble includes 2E=16 responses. The initial few sequences (perhaps 2 sequences) should be rejected as a start-up transient for each initiation of data acquisition. This controls for transient behavior in the middle-ear reflex at the onset of the stimulus. Stopping rules may be specified, either in terms of a minimum number of acceptable ensembles or in terms of a signal-to-noise criterion.

Nonlinear Coherence

The purpose of any EOAE measurement is to extract the signal representing evoked cochlear energy, but the measured response is degraded by nonlinear distortion in the measurement apparatus and by random noise. Contributors to random noise include physiological noise that is sensed by the microphone in the ear canal, mainly due to respiration, circulation and vocalizations, electrical noise in the instrumentation, and ambient environmental noise in the room in which the measurements are made. By averaging the response, it is usually possible to reduce the random noise components, although this depends somewhat on the long-term characteristics of the random noise, since changes in the physiologic state of the patient or human subject can elevate the noise floor.

Distortion may occur in the probe assembly due to nonlinearities in the microphone or nonlinearities in the source. Related distortion categorized for present purposes as "probe distortion" includes distortion in the DAC or ADC. The most significant nonlinearity in the probe is typically associated nonlinearities in the acoustic source(s) 130 and 132, that are most important as nonlinearities in transients near peak excitation levels. This has been assumed in the discussion of the double-source reduction in probe distortion, but it must be recognized that other nonlinearities may also contribute to total probe distortion. Nonlinear distortion is not significantly influenced by averaging. Nevertheless, an essential first step is to extract the deterministic portion of the total measured response from the randomly varying portion of the response.

This section describes a new technique to reduce random noise, denote herein as "noise". Noise reduction is essential in practical measurement systems because EOAEs are so low in level. A variety of noise reduction techniques have been applied in CEOAE and DP measurement systems. CEOAE techniques have collected time averages in 2 or more sub-ensembles of responses, each sub-ensemble corresponding to a time-domain average of a number of individual click responses. The waveforms from any pair of sub-ensembles can be cross-correlated to calculate the reproducibility of the response, as discussed by Probst et al., "A Review of Otoacoustic Emissions," *J. Acoust. Soc. Am.* 89:2027–2067, 1991, but this technique is not sensitive to the frequency-specific character of physiologic noise, which occurs mainly at low frequencies for respiratory and circulatory noise. The cross-spectrum of two sub-ensembles, calculated in the frequency domain using the DFT of the response, has been used to calculate the CEOAE spectra, but this does not allow an independent estimate of the random noise level. One approach to measuring the random noise spectrum is to simply subtract the spectra calculated from a pair of sub-ensemble measurements, and convert this difference spectrum to a sound pressure level. This subtraction procedure is not related in the prior art to a rigorous definition of random noise, as found using nonlinear coherence analysis.

DP measurement systems have estimated noise by taking advantage of the frequency specificity of the DP response to two sinusoidal tones. When the response is transformed to the frequency domain using a DFT, each individual DP components resides in a separate spectral bin, whose center frequency is close to the DP frequency. Noise is estimated by comparing the level in the DP bin with the levels in the adjacent frequency bins that do not contain the DP. Alternatively, noise can be estimated from separate sub-ensembles in the DP bin itself, by calculating the difference spectrum. Since the 2ChDP response is broad band rather than narrow band as in conventional DP techniques, it is not possible to identify a specific frequency bin associated with a single DP over the duration of the stimulus.

There exist well-known techniques for obtaining independent estimates of signal level and random noise level from experimental data, which are referred to as coherence estimation methods, as described in Bendat, *Nonlinear System Analysis and Identification From Random Data*, 2nd ed. Wiley, New York, 1990 ("Bendat (1990)"). These are based upon the use of cross-spectral and autospectral measurements in the frequency domain upon subensembles of responses. Intuitively, the random noise is uncorrelated with the deterministic stimulus used to evoke a response. It follows that the random noise and the evoked deterministic response in the ear canal are incoherent. These techniques can be applied to the general case of a measured 2EOAE response, and are thus applicable to each particular embodiment. Because the 2EOAE response is nonlinear, it is necessary to define a nonlinear coherence.

The signal level, expressed in decibels, is equal to ten times the common logarithm of the signal autospectrum, and the noise level is similarly proportional to the noise autospectrum. The autospectrum is defined in Bendat (1990), and corresponds to what is often called in signal processing the "power" or "energy" calculated from the noise autospectrum. This terminology is not used herein, because the term power is reserved for the physical concept of power. The purpose of coherence estimation is to obtain separate estimates of the signal autospectrum and the noise autospectrum.

Coherence estimation is formulated in the frequency domain. It is convenient to adopt a separate notation in this section. At frequency $f$, the stimulus input to the acoustic source 130 (see FIG. 2) is $X(f)$, and the response output measured by the microphone 134 is $Y(f)$. It is assumed that the microphone 134 has linear response and negligible internal noise. The linear transfer function between stimulus and response is $H(f)$. This transfer function takes account of the frequency response of the acoustic source 130 and microphone 134, and the linear response of the external, middle and inner ear to stimulus presentation at the probe tip 140a. The signal $H(f)X(f)$ linearly contributes to the measured output $Y(f)$. There are two additional outputs that are assumed. One is random measurement noise $R(f)$, due to acoustic source transducer noise, physiologic and environmental noise. The signal $R(f)$ is uncorrelated with $X(f)$. Another is a nonlinear distortion signal $D(f)$, that has two components, nonlinearity in the probe and nonlinearity in the ear (i.e., the EOAE).

The output signal is $$Y(f)=H(f)X(f)+R(f)+D(f). \tag{23}$$

The technique of cross-spectral estimation, described in Bendat (1990), is used to calculate the coherence. The technique depends upon the existence of separate ensembles of measurements. Ensemble averaging is used, such that $G_{uv}$ denotes the cross-spectrum between any pair of signals $U(f)$ and $V(f)$, and $G_{uu}$ denotes the autospectrum of $U(f)$.

The cross-spectrum $G_{xy}$ of the input and output signals is calculated from the above equation (23) to be $$G_{xy}(f)=H(f)G_{xx}(f)+G_{xr}(f)+G_{xd}(f)=H(f)G_{xx}(f)+G_{xd}(f). \tag{24}$$

The cross-spectrum of the input signal with the noise is zero, $G_{xr}=0$, since $R(f)$ is uncorrelated with the input signal as discussed above. $G_{xd}$ is the cross-spectrum of the input with the nonlinear distortion signal $D(f)$. The frequency response function $\hat{H}(f)$ of the system is defined as $$\hat{H}(f) = \frac{G_{xy}}{G_{xx}} = H(f) + \frac{G_{xd}}{G_{xx}}. \tag{25}$$

This demonstrates that the frequency response of the system is biased by the presence of distortion, since $\hat{H}(f)$ does not equal $H(f)$.

Examples of calculations of the nonlinear coherence function are given for the general case for this system in Maki, "Interpretation of the Coherence Function When Using Pseudorandom Inputs to Identify Nonlinear Systems," Trans. Biomed. Engr. BME-33:775–779, 1986. In the present application, a subtraction procedure is carried out to remove the linear response of the system. Applying this subtraction procedure to the nonlinear coherence analysis results in a much simpler nonlinear coherence function than in the prior art. This is accomplished by subtracting the linear system response, $H(f)X(f)$, from both sides of equation (23), defining the new nonlinear variable $\tilde{Y}(f)$ by $$\tilde{Y}(f)=Y(f)-H(f)X(f)=R(f)+D(f) \tag{26}$$

Thus, the cross-spectrum $\tilde{G}_{xy}$ of $X(f)$ with $\tilde{Y}(f)$ $$\tilde{G}_{xy}=G_{xy}-HG_{xx}=G_{xd}. \tag{27}$$

The autospectrum of $\tilde{Y}(f)$ is $$\tilde{G}_{yy}=G_{dd}+G_{rr}. \tag{28}$$

since the noise is uncorrelated with the deterministic distortion. Equation (28) states that the total measured autospectrum measured at the output, after subtracting off the linear response, is the sum of the distortion signal autospectrum and the noise autospectrum.

The nonlinear coherence function $\gamma^2$ is defined by $$\gamma^2 = \frac{|\tilde{G}_{xy}|^2}{G_{xx}\tilde{G}_{yy}} \tag{29}$$

and quantifies the ratio of the output nonlinear power $\tilde{G}_{yy}$ that is coherent with the input power $G_{xx}$. The nonlinear coherence varies between zero and unity. A calculation of this coherence from the above definition leads to the following relation:

$$\gamma^2 = \frac{G_{dd}}{G_{dd} + G_{rr}}. \tag{30}$$

This is the key result. The nonlinear coherence is equal to the ratio of the distortion power to the sum of the distortion and the noise autospectra, which, from equation (28) is the total response autospectrum $\tilde{G}_{yy}$. Equation (30) is used to generate the distortion signal to noise ratio, the coherent distortion autospectrum and the noise autospectrum. Before presenting these relations, the method of calculating nonlinear coherence from the sampled data is summarized.

The nonlinear coherence is implemented using equation (29). The autospectra are calculated by a sum (i.e., ensemble average) over K statistically independent measurements of the underlying variables $X_i$ and $\tilde{Y}_i$, $i$ ranging from $1, \ldots,$ K. An important simplification occurs because the input variable is the stimulus $X(f)=S_1(f)$, which is precisely known. The cross-spectrum and autospectra are calculated using $$\tilde{G}_{xy}(f) = (1/K) \sum_{i=1}^{K} X_i^*(f)\tilde{Y}_i(f) = (1/K)S_1^*(f) \sum_{i=1}^{K} \tilde{Y}_i(f), \tag{31}$$

$$\tilde{G}_{yy}(f) = (1/K) \sum_{i=1}^{K} |\tilde{Y}_i(f)|^2,$$

$$G_{xx}(f) = (1/K) \sum_{i=1}^{K} X_i^*(f)X_i(f) = |S_1(f)|^2,$$

where the asterisk denotes the complex conjugation operation. The random-error variances of the autospectra and cross-spectrum are proportional to $1/K$. Thus, increasing the number of averages increases the accuracy of the spectral estimation.

One important fact is that averaging over frequency is equivalent to averaging over ensembles, since random noise is uncorrelated across frequencies. Thus, the variance of estimating the auto- and cross-spectra can be reduced by averaging over adjacent frequencies. It is typical for hearing applications to average over the log frequency axis. The results below demonstrate that ⅓-octave averaging is sufficient to obtain adequate signal-to-noise, but octave averaging provides for even larger signal-to-noise, and is sometimes desirable for hearing screening applications and might be desirable for some clinical applications in hearing.

The resulting coherence, with the substitutions $S_1(f)=X(f)$ and $P_D(f)=\tilde{Y}(f)=P_{12}(f)-[p_1(f)+p_2(f)]$, is $$\gamma^2(f) = (1/K) \frac{\left| \sum_{i=1}^{K} P_D(f) \right|^2}{\sum_{i=1}^{K} |P_D(f)|^2} . \quad (32)$$

Equation (32) is the desired result for the coherence, calculated from the sampled pressure signal in the ear canal or coupler.

The nonlinear signal-to-noise ratio, termed the distortion-to-noise ratio DNR is defined in terms of coherence by $$DNR = \frac{\gamma^2}{1-\gamma^2} . \quad (33)$$

Thus, the signal to noise ratio is large when the coherence approaches unity, and small when the coherence approaches zero. The DNR evaluates to $$DNR = \frac{G_{dd}}{G_{rr}} , \quad (34)$$

which is precisely the intuitive notion of nonlinear signal to noise. It is numerically evaluated from equations (32) and (33).

It is evident from equations (28) and (30) that the coherent distortion autospectrum $G_{dd}$ is calculated from the product of the coherence function and the total autospectrum $\tilde{G}_{yy}$. It is further evident that the noise spectrum is calculated from the product of $(1-\gamma^2)$ and the total autospectrum $\tilde{G}_{yy}$.

This concludes the decomposition of the measured nonlinear response into a deterministic component and a random component. It must be cautioned that there the EOAE measurement system can provide both absolute reproducibility and meaningless data. If the coherence is close to unity, then the random noise power is negligible, but there remain two components to distortion, probe and cochlear distortion. In practice, measurements in a calibration tube, for example, the 1-cc coupler, should provide the distortion power due to probe and other system nonlinearities. When an EOAE response is measured (CEOAE, DPOAE, 2ChDP or 2CEOAE), the nonlinear coherence should be high and the distortion power should be significantly larger than that in the calibration tube, in order to validate that a response has a physiologic component.

A final factor is to account for impedance differences between the coupler and the ear canal, so that the distortion in both the coupler and ear are compared with respect to acoustic power absorption.

The criterion for deciding that an OAE is present (any EOAE or DPOAE) is chosen in the manner outlined below. Measurements are obtained in a 1-cc coupler or other calibration cavity that mimics some properties of the ear, and also in the ear. The nonlinear coherence is calculated so that confidence limits are constructed using well-known techniques for detecting a deterministic signal in random noise, as discussed in Bendat (1990). The fractional sub-division of the octave can be varied to increase the number of ensemble averages, and, thereby, more easily attain a given confidence limit. Multiple regression, or, equivalently, analysis of variance, is performed to test whether the EOAE response exceeds that of the calibration cavity response. If a significant difference exists, then well-known multiple comparison tests can further be used to identify particular octaves or sub-octaves in which EOAE responses are significantly larger than probe distortion responses.

Regarding stimulus design, the stimulus spectrum $A(f)$ may be carefully shaped to minimize probe distortion, because the clipping type of nonlinearity is mainly a low-frequency nonlinearity. Thus, frequencies below the 2EOAE measurement range to minimize probe distortion, but $A(f)$ is maintained at sufficiently high levels at higher frequencies to provide adequate nonlinear signal-to-noise ratio. Measurements of acoustic conductance (Keefe et al. (1993)) are useful to identify the presence of standing wave nodes near the probe tip 140a (see FIG. 2). All these responses are combined to give an improved spectral shaping of the stimulus $A(f)$.

Real-Time Artifact Rejection

Artifact rejection is the elimination of exceptionally noisy data from the measured response. Such exceptional events are due to large-amplitude spikes in physiologic and environmental noise, and occasional glitches in the electronics. The methods of time averaging and ensemble averaging are conventionally used to remove such noise components, but it is preferable to detect the existence of exceptional events before the corresponding responses are added to the averaging process. Such a technique needs to operate in real time, which means sufficiently rapidly that responses containing such artifacts can be detected and excluded during the process of data acquisition. Such a real-time artifact rejection method is of undoubted importance in hearing screening and related clinical applications, because valid data may be acquired in much shorter times by the exclusion of bad responses. Moreover, a real-time artifact rejection technique may lead to the acquisition of valid data when all other techniques fail, because it is able to capture individual "good" responses even in the presence of large-amplitude, but intermittent, noise.

The technique is implemented on the DSP 121 (see FIG. 1), which is the real-time controller of stimulus output via the DAC 120, response input via the ADC 116, time-averaging of responses, and communication with the CPU 102. The DSP 121 acquires the current buffer of response data from the ADC 116 and compares it, sample by sample, to the previous buffer of data that is stored in the DSP memory (not shown). The magnitude of the difference between the current and previous buffer is compared to some threshold value. If this magnitude difference is less than the threshold at all sample values, then the current buffer is accepted as valid data. It is incremented to the sum used to calculate the time-domain average, and it is copied to the previous buffer memory location. The cycle repeats with the acquisition of a new buffer.

If the magnitude difference exceeds the threshold at any sample value, then the current buffer is rejected as artifact, that is, it is not incremented to the sum used to calculate the time-domain average and it is not copied to the previous buffer memory location.

The essential idea is the comparison of the current response buffer to some previous response, which might also be the running sum of the previous valid responses, and to reject the current buffer if it exceeds some error threshold. The real-time nature of the artifact rejection is one of the novel components of this part of the invention.

This method detects the presence of intermittent noise very effectively. It is further possible to output the maximum magnitude difference value across all samples from the DSP 121 to the CPU 102 without stopping data acquisition, and the operator can thereby monitor a real-time record of maximum error. It is further possible for the operator to interactively vary the error threshold level during data acquisition based upon the maximum magnitude difference values that the operator is observing on the computer monitor. In testing this technique, it is possible to sensitively set this threshold so that EOAE responses are rejected during the inspiratory phase of respiration, which tends to elevate the physiologic noise measured in the ear canal, and accepted during the expiratory phase of respiration. Such a real-time artifact rejection method was used to acquire the responses shown in FIGS. 14A and 14B. Overall measurement time is reduced, and this promises application to the much nosier respiratory cycle of neonates.

It is obvious to one skilled in the art of DSP programming, that other similar threshold rejection measures might be used. For example, the Implementation Section above describes a single response which is actually composed of the response to two stimulus presentations. The response is partitioned into two responses so that two sub-ensembles of responses can be collected. Rather than comparing the current buffer to the previous buffer, it is obvious that the first sub-ensemble of the current buffer might be compared to the second sub-ensemble of the current buffer. The resulting real-time artifact rejection would be substantively similar. Instead of the magnitude difference function, any other norm of the difference between two response may alternatively be employed.

2CEOAE Response Results

The conventional CEOAE responses and the 2CEOAE responses of the system 100, time-averaged over 128 presentations, were measured using procedures described above, and digitally filtered below 400 Hz to attenuate low-frequency noise. The conventional CEOAE responses, using the standard 1-up, 3-down stimulus of FIG. 4, are illustrated in FIGS. 8A to 8D.

The electrical input was in the up-state for 2 samples, or 125 $\mu$s. FIG. 8A illustrates the waveform response to the conventional CEOAE stimuli in the 1-cc coupler. FIG. 8B is the identical response with the vertical scale magnified. FIG. 8C illustrates the response to the conventional CEOAE stimuli in the ear. FIG. 8D is the identical response with the vertical scale magnified.

The probe nonlinearity was clearly present in both the 1-cc coupler (FIGS. 8A and 8B) and in the ear (FIGS. 8C and 8D) over the initial 64 samples (approximately 4 msec). It is this early part of the CEOAE that is conventionally nulled in order to obtain a meaningful response.

Figure 9A:
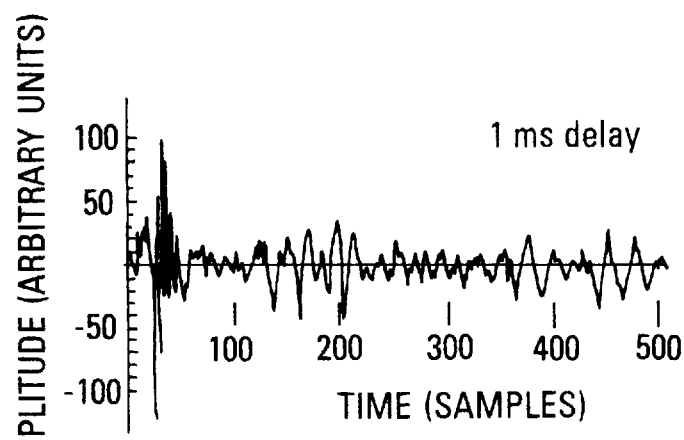
FIGS. 9A to 9C are waveforms of the double-click evoked emission stimulus response of the system of FIG. 1 to the stimulus of FIGS. 3A to 3C.
Figure 9B:
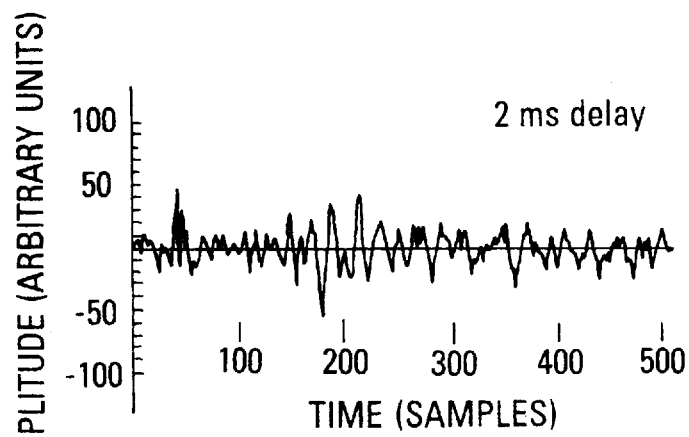
Figure 9C:
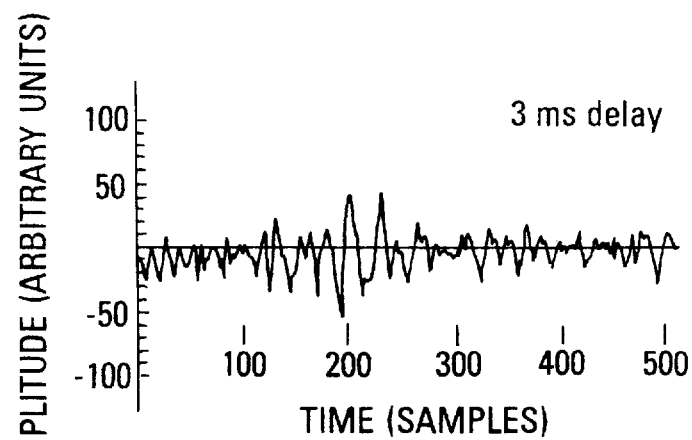

The response to the 2CEOAE stimulus of the system 100 is significantly different from that of the conventional CEOAE. The 2CEOAE responses of the system 100 in the ear were also significantly larger than those in the 1-cc coupler. The 2CEOAE stimuli of the system 100 are illustrated in FIGS. 3A to 3C for time delays ranging from 1–3 msec. The responses in the ear to the 2CEOAE stimuli of FIGS. 3A to 3C are illustrated in FIGS. 9A to 9C, respectively. As seen in FIGS. 9A to 9C, the probe distortion in the early latency response is significantly reduced compared with the conventional CEOAE responses shown in FIGS. 8A to 8D.

The more interesting comparison emerges across the range of time delays used to construct the stimuli. For a 1 msec time delay, there is a large-amplitude spike in the response at early latencies, shown in FIG. 9A, which corresponds to probe distortion. This same effect was observed in the 1-cc coupler responses. As the time delay increases to 2 and 3 msec, the probe distortion completely disappears, as shown in FIGS. 9B and 9C. Even at a time delay of 1 msec, the probe distortion is only 3% in peak amplitude of the probe distortion in the conventional CEOAE measurement of FIG. 8C. The conclusion is that the probe nonlinearity is reduced by a factor of 30 in the 2CEOAE measurement relative to that in the conventional CEOAE measurements.

2ChDP Response Results

Figure 10A:
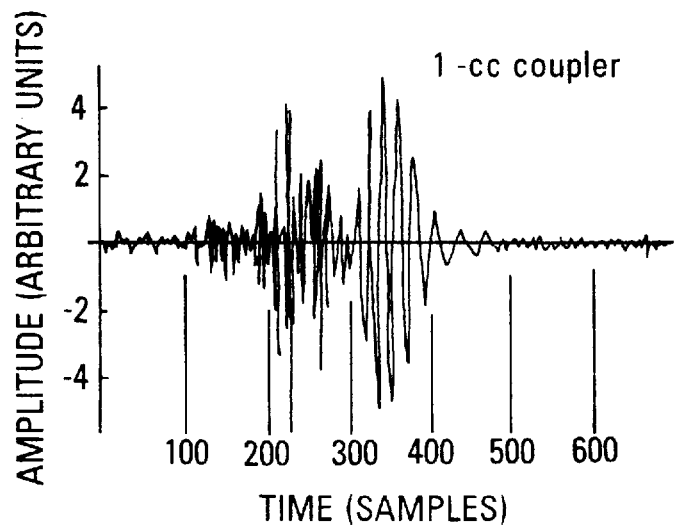
FIGS. 10A to 10B are waveforms of the double chirped evoked emission stimulus response of the system of FIG. 1 to the stimulus of FIG. 6A.
Figure 10B:
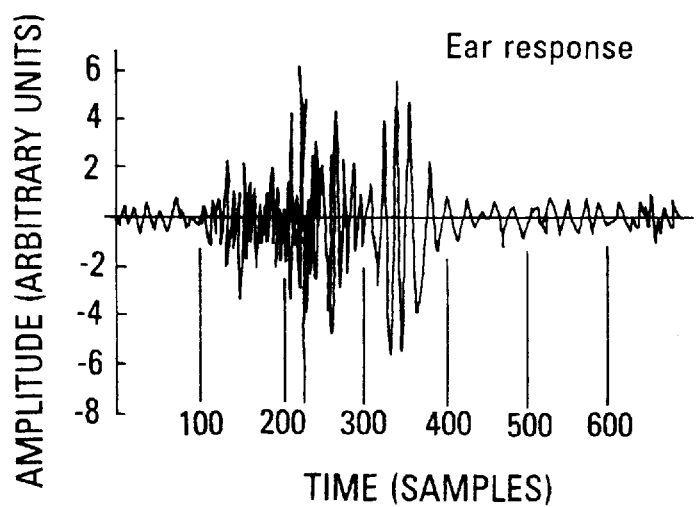

The 2ChDP responses using the stimuli of FIGS. 6A to 6C are illustrated in FIGS. 10A and 10B for the measurement in the 1-cc coupler and in the ear, respectively. These measurements differed from the preceding 2CEOAE measurements in that the responses were lowpass filtered using a Krohn-Hite analog filter (not shown) with a cutoff frequency of 400 Hz before digitization by the ADC 116 (see FIG. 1). These responses were 64 averages of each of two sub-ensembles of responses. The response in the ear was significantly larger than that in the coupler-note the different amplitude scales in FIGS. 10A and 10B.

Figure 11A:
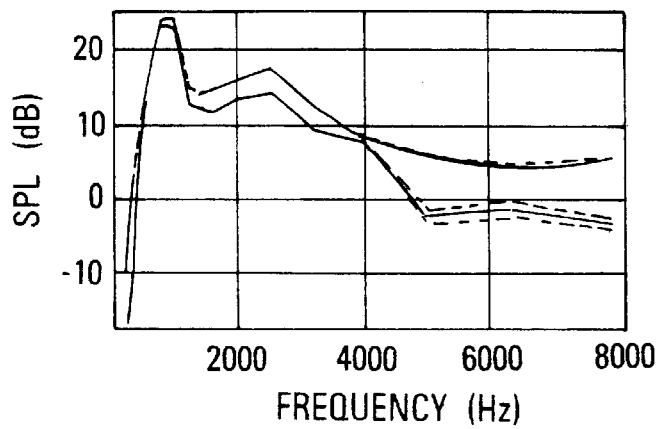
FIGS. 11A to 11C are power spectra of the double chirped evoked emission stimulus responses of the system of FIG. 1 to the stimulus of FIGS. 6A to 6C.
Figure 11B:
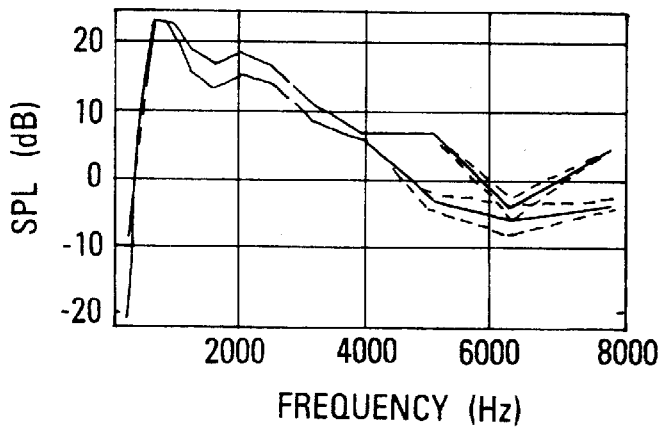
Figure 11C:
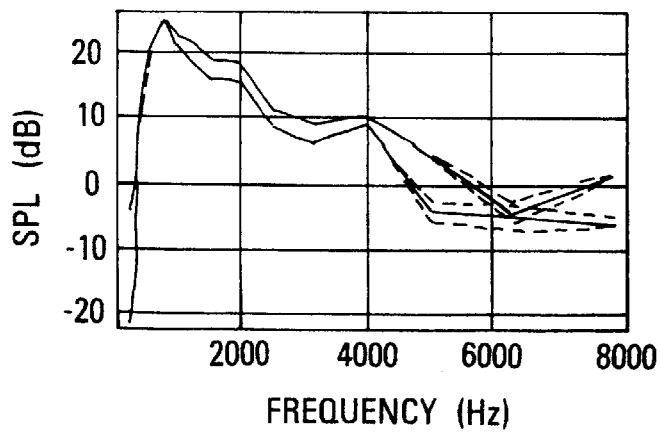

The chirp spectra were calculated along with the distortion signal-to-noise ratio DNR. FIGS. 11A to 11C plots the 2ChDP spectra (dB SPL) in solid lines using the relation SPL=20 log $(P_D/P_0)$, where $P_0=2\times10^{-5}$ Pa. The dashed lines above and below the solid line plot 20 log $[(P_D/P_0)(1+1/\sqrt{DNR})^{\pm\frac{1}{2}}]$, respectively. The three plots of FIGS. 11A to 11C illustrate the 2ChDP response for 1 msec, 2 msec, and 3 msec time delays, respectively. There are two sets of measurements on each of the three plots of FIGS. 11A to 11C. One set corresponds to the ear measurement and the other to the 1-cc coupler measurement. The 1-cc coupler measurements, along with its noise range, were always lower in level than the ear measurements.

The nonlinear coherence method discussed above with respect to equations (23) to (34) effectively de-coupled the separate influences of random noise from probe distortion. The signal-to-noise ratio was always larger for the ear measurements than the coupler measurements, because the EOAE response was larger. The coupler measurements demonstrated that probe distortion was significant, particularly at low frequencies (500–2000 Hz). This is illustrated in FIGS. 11A to 11C by the near intersection of the responses from the 1-cc coupler and the ear, indicating that the response is not caused by the ear, but by probe nonlinearities. This is where $A(f)$ could be reduced to lessen the overall distortion. From 5000–8000 Hz, the coupler measurements indicate that random noise was a significant limiting factor, because the dashed lines are observed to deviate from the mean. This directly shows the reduction in distortion noise power to random noise power (see equation (34)). This is where $A(f)$ could be increased to reduce the influence of random noise.

The most interesting feature of these plots is the structure of the 2ChDP emission as the inter-stimulus time delay is varied. With a 1 msec time delay, the 2ChDP emission, shown in FIG. 11A, was clearly present from the third octave above 1 kHz to the third octave just below 8 kHz. With 2 and 3 msec time delays, the 2ChDP emission, shown in FIGS. 11B and 11C, respectively, was present at slightly lower frequencies (in the 1 kHz third-octave) because of a reduction in probe distortion, but there was a notch in the 2ChDP emission at 6.3 kHz. These results are very promising because they have been obtained with a single source, for which probe distortion effects were significant.

Figure 12A:
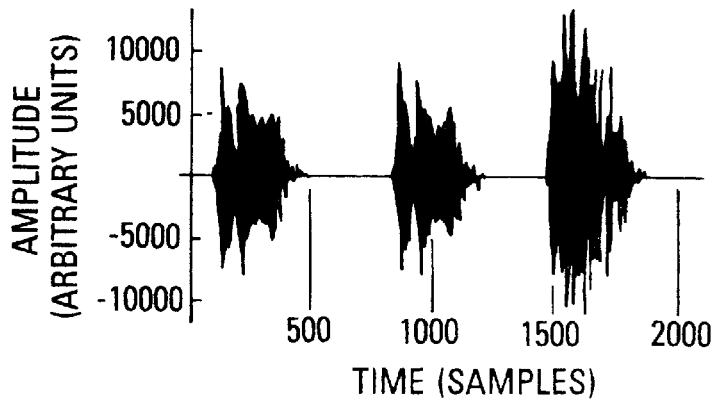
FIG. 12A is a waveform of the double chirped evoked emission stimulus response of the system of FIG. 1 to the chirped stimulus of FIG. 6C.
Figure 12B:
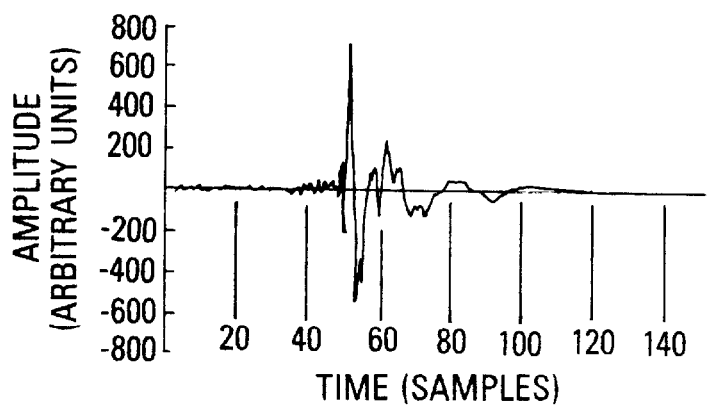
FIGS. 12B to 12D are dechirped responses to the double chirped evoked emission stimulus response of the system of FIG. 1 to the chirped stimulus of FIG. 6C.
Figure 12C:
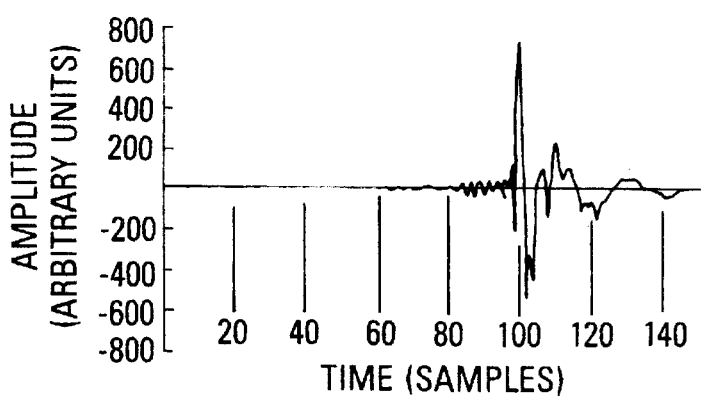
Figure 12D:
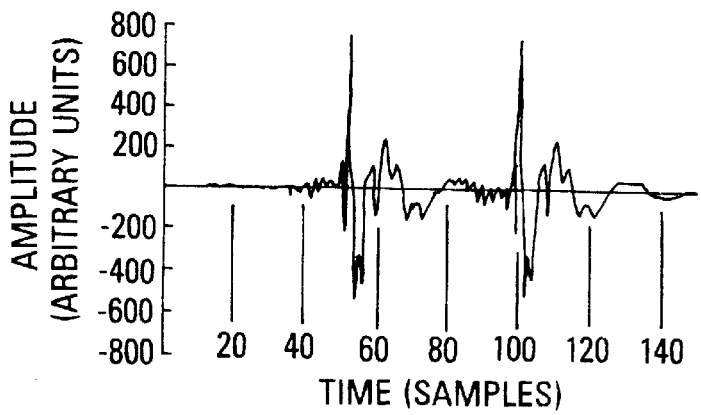
Figure 13A:
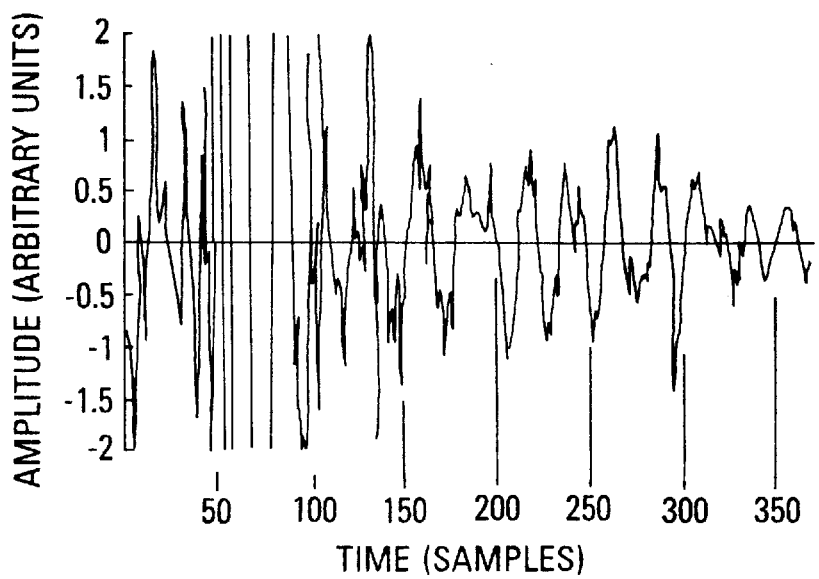
FIG. 13A is a waveforms of the difference response illustrating the nonlinear response to the chirped stimulus of FIG. 6C.

FIGS. 12A to 12D show intermediate stages in the signal processing by the system 100. The plot in FIG. 12A illustrates the 2ChDP chirp response in the ear for time delay $\tau_m=3$ msec. The plots of FIGS. 12B to 12D show the dechirped responses $d_1(t)$, $d_2(t)$ and $d_{12}(t)$, respectively, calculated from equations (18) and (19) over their initial 150 samples (approximately 9.4 msec). The equivalent peak amplitude of 800 milliPascals (mPa) corresponds to a peak equivalent level of 92 dB SPL. The 3 msec (i.e., 48 sample) delay is obvious in the $d_{12}$ waveform. The actual peak levels in the ear canal were much lower due to the use of the chirp stimulus. The difference $d_D(t)=d_{12}(t)-[d_1(t)+d_2(t)]$ is illustrated in the plot of FIG. 13A. There is a large-amplitude response at early latencies in the dechirped response. This is a manifestation of probe nonlinearity, which would be reduced by using a pair of acoustic sources 130 and 132 (see FIG. 2). Nevertheless, the probe distortion is sufficiently small to have enabled adequate detection of the 2ChDP emission in FIG. 11C over a broad range of frequencies.

Figure 13B:
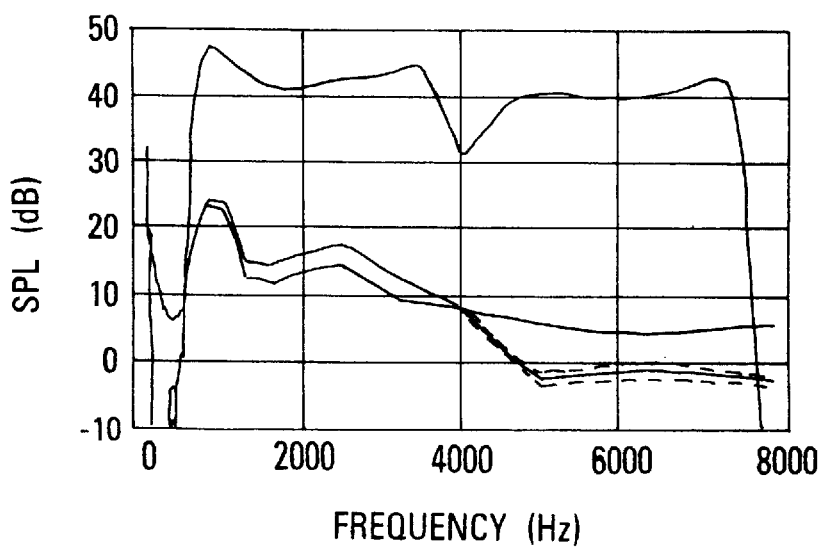
FIG. 13B are power spectra of the double chirped evoked emission stimulus responses of the system of FIG. 1 to the stimulus of FIG. 6C.

The plot in FIG. 13B re-draws the 2ChDP spectrum for time delay $\tau_m=1$ msec along with the total ear-canal level (narrow-band spectrum rather than ⅓-octave averaged) produced by the $S_1(f)$ stimulus (i.e., 20 log $(P_1/P_0)$). At low frequencies near 800 Hz, there is a maximum in the ear-canal level of 48 dB SPL that correlates to the peak distortion in the probe nonlinearity. The ear-canal pressure level is reduced near 4000 Hz due to the corresponding peak in the conductance G, but the power levels are fairly flat so that the emission level is also fairly flat.

Double-Source, Zero Time-Delay Variant of 2CEOAE Response Results

The 2CEOAE stimuli were constructed with equal amplitude ($\epsilon=1$) and zero time delay ($\tau=0$), but a double-source configuration was used. This means that each acoustic source 130 and 132 (see FIG. 2) outputs an identical click simultaneously that is acoustically mixed within the ear canal or coupler to form a single click. It was predicted that this stimulus with the subtraction method described above leads to reduced probe distortion as well as the ability to measure an OAE without the use of conventional time-gating. This case is called the double-source 1CEOAE, since there is a single acoustic click produced by signal processing from a pair of clicks.

Figure 14A:
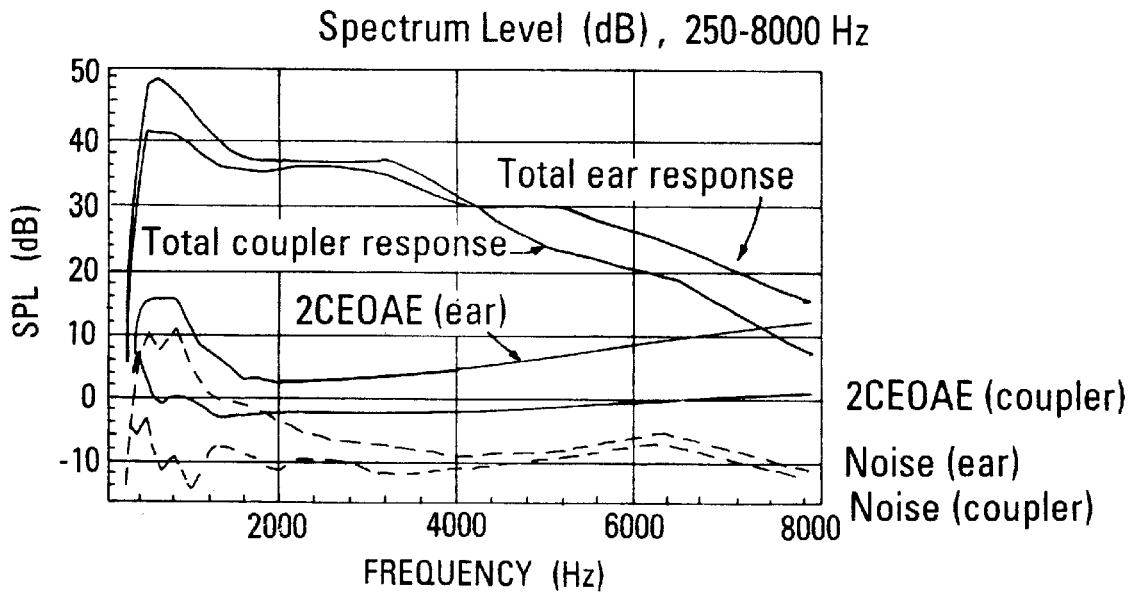
FIGS. 14A and 14B are power spectra of the double-clicked evoked emission stimulus responses of the system of FIG. 1 to a double-source single click.
Figure 14B:
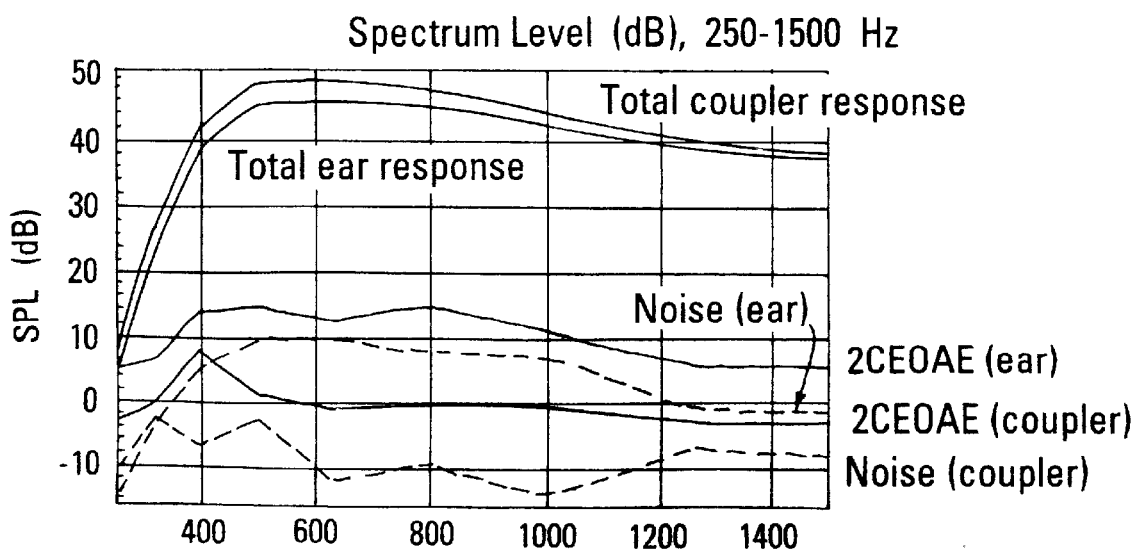

The results in FIGS. 14A and 14B confirm this prediction. The plot of FIG. 14A shows the SPL versus frequency from 250–8000 Hz for six response functions. All response functions are averaged over each ⅓-octave as part of the nonlinear coherence method of noise reduction. The largest-SPL pair (solid lines) are the total responses to the stimulus $s_1(t)$ presented in the ear canal and the 1-cc coupler. The 2CEOAE pair (solid lines) are the total distortion signal measured in the ear canal and the coupler. The noise SPL pair (dashed lines), calculated using the noise autospectrum from the coherence analysis described above, show the random noise in the ear canal and coupler. This representation of the noise level is a contrasting representation of the data to the distortion signal to noise level presented in FIGS. 11A to 11C. The plot of FIG. 14B shows the same six response functions plotted over the low frequency range from 250–1500 Hz.

A valid double-source 1CEOAE response in the adult ear was obtained from 250–8000 Hz, because this response exceeds the noise level in the ear in each ⅓-octave and exceeds the deterministic probe distortion in the 2CEOAE coupler response. This coupler response is at least 4 dB above its noise level at all but a single third-octave (near 300 Hz). There is no need for timegating in calculating this response. The double-source 1CEOAE response is obtained at both higher and lower frequencies than that reported in the prior art for CEOAE responses. The excellent signal to noise obtained at low frequencies is due to the elimination of significant amounts of probe distortion, whereas at high frequencies is due to the fact that time gating was not applied to the CEOAE response, which results in the elimination of the short-latency, high-frequency cochlear responses.

This demonstrates the advantage of the techniques provided by the system 100. Such advantages are important in clinical applications of click-evoked otoacoustic emission measurement systems, and should be particularly important for testing infants, since the physiologic noise is much higher in infants than adults.

The system 100 provides new sets of stimuli that overcome significant drawbacks of the existing technology. The techniques used to reduce probe nonlinearities permit the measurement of short latency responses that could not previously be analyzed. Furthermore, the novel techniques for analyzing nonlinear coherence provide an accurate quantitative measure of random noise and distortion noise.

It is to be understood that even though various embodiments and advantages of the present invention have been set forth in the foregoing description, the above disclosure is illustrative only, and changes may be made in detail, yet remain within the broad principles of the invention. Therefore, the present invention is to be limited only by the appended claims.

What is claimed is:

1. A system for the measurement of the nonlinear coherence of an evoked otoacoustic emission, the system comprising:

a probe assembly, insertable in the ear, to generate an acoustic stimulus signal in response to an electrical stimulus signal;

an acoustic transducer to convert detected acoustic energy to detected electrical signals, said acoustic detector detecting an acoustic response signal from the ear in response to said acoustic stimulus signal and generating an electrical response signal corresponding to said acoustic response signal, said acoustic response signal comprising a linear portion, a nonlinear portion and a random noise portion, said nonlinear portion comprising a distortion portion and a cochlear response portion;

a correlation analyzer to receive said electrical response signal and to calculate a cross-spectrum of said electrical stimulus signal and said electrical response signal, said correlation analyzer calculating a nonlinear coherence value indicative of an amount of power in said electrical response signal due to said cochlear response portion compared to an amount of power in said electrical response signal due to said random noise portion.

2. A system for the use of artifact rejection, comprising:

an acoustic transducer to convert detected acoustic energy to detected electrical signals, said acoustic detector detecting an acoustic response signal in response to an acoustic stimulus signal and generating an electrical response signal corresponding to said acoustic response signal;

an analog to digital converter coupled to said acoustic transducer to convert said electrical response signal to a digital electrical response signal comprising a plurality of digitized data samples;

a first buffer accepting said digital electrical response signal corresponding to a first acoustic stimulus signal;

a second buffer accepting said digital electrical response signal corresponding to a second acoustic stimulus signal; and a processor to accept said first buffer as valid data, said processor calculating a difference between each of said digitized data samples in said first data buffer a corresponding digitized data sample in said second data buffer and accepting said second buffer as valid data only if each of said differences between said first and second digitized data samples is less than a predetermined threshold.

3. The system of claim 2 wherein said processor determines a maximum difference value for said differences between said first and second digitized data samples.

4. A system for the generation of an evoked otoacoustic emission stimulus signal and for the measurement of an evoked otoacoustic emission response in a human ear canal, the system comprising:

a signal generator to generate a first stimulus having a first arbitrary waveform and a second stimulus signal having a second arbitrary waveform, each of said first and second stimulus signals having the same elementary duration;

said signal generator generating an electrical three-stimulus signal comprising said first stimulus signal in a first time interval, said second stimulus signals in a third time interval, said electrical three-stimulus signal having a three-stimulus duration three times that of said elementary duration;

a probe assembly, insertable into the ear canal, including a source transducer coupled to said signal generator to receive and transduce said electrical three-stimulus signal into an acoustic three-stimulus signal for stimulating an evoked otoacoustic emission response;

said probe assembly including an acoustic transducer to convert detected acoustic energy into an electrical response signal with said three-stimulus duration corresponding to said detected acoustic energy; and a processor coupled to said acoustic transducer to receive said electrical response signal and to determine therefrom an evoked otoacoustic emission response;

said evoked otoacoustic emission response being calculated by the processor by partitioning said electrical response signal into a first-interval response signal in said first time interval, a second-interval response signal in said second time interval, and a third-interval response signal in said third time interval, and calculating said evoked otoacoustic emission response by subtracting said first-interval response signal and said second-interval response signal from said third-interval response signal.

5. The system of claim 4 wherein said first and second stimulus signals are first and second chirp signals, respectively, said first chirp having a first predetermined group delay, and said second chirp signal having a second predetermined group delay, said first and second group delays having a predetermined relationship.

6. The system of claim 5 wherein said second group delay is a predetermined multiple of said first group delay.

7. The system of claim 5 wherein said first and second chirp signals are linear chirp signals with said first and second group delays each being a linear function of frequency.

8. The system of claim 5 wherein said first and second chirp signals are logarithmic chirp signals with said first and second group delays each being a logarithmic function of frequency.

9. The system of claim 5 wherein said first chirp signal is related to said second chirp signal such that each frequency of said second chirp signal at a given point in time is a fixed multiple of each frequency of said first chirp signal at said given point in time.

10. The system of claim 9 wherein said first group delay at a selected frequency is selected to equal said second group delay at a frequency equal to said selected frequency multiplied by said fixed multiple.

11. The system of claim 5 wherein said source transducer produces first and second acoustic chirp signals in response to said first and second chirp signals, respectively, said acoustic transducer detecting an acoustic chirp response signal from the ear in response to the first and second acoustic chirp signal corresponding to said acoustic chirp response signal; and said processor being coupled to said acoustic transducer to receive said electrical chirp response signal and to determine therefrom an evoked cochlear response to said first and second acoustic chirp signals.

12. The system of claim 11, further including an inverse allpass filter within said processor to convert said electrical chirp response signal into a dechirped electrical response signal indicative of a cochlear response to click signals.

13. The system of claim 4 wherein said first and second stimulus signals are first and second click signals, respectively.

14. The system of claim 4 wherein said first arbitrary waveform generated by said signal generator is characterized by a first amplitude, and said second arbitrary waveform having a waveform shape identical to said first arbitrary waveform except for a second amplitude with arbitrary value, and a relative delay time.

15. The system of claim 14 wherein said second amplitude and said first amplitude are substantially equal.

16. The system of claim 14 wherein said delay time ranges from 0 to 10 milliseconds.

17. The system of claim 4 wherein the probe assembly contains a static pump that modifies the static pressure in the ear canal, and the evoked otoacoustic emission response is measured at one or more static pressures.

18. A system for the generation of an evoked otoacoustic emission stimulus signal and for the measurement of an evoked otoacoustic emission response in a human ear canal, the system comprising:

a signal generator to generate a first stimulus signal having a first arbitrary waveform, a second stimulus signal having a second arbitrary waveform, and a zero stimulus signal, each of said first, second and zero stimulus signals having the same elementary duration; and said signal generator generating a first electrical three-stimulus signal comprising said first stimulus signal in a first time interval, said zero stimulus signal in a second time interval, and said first stimulus signal in a third time interval, and generating a second electrical three-stimulus signal comprising zero stimulus signal in said first time interval, said second stimulus signal in said second time interval, and said second stimulus signal in said third time interval, said first and second electrical three-stimulus signals having a three-stimulus duration three times that of said elementary duration;

a probe assembly, insertable into the ear canal, including a first source transducer coupled to said signal generator to receive and transduce said first electrical three-stimulus signal, and a second source transducer coupled to said generator to receive and transduce said first electrical three-stimulus signal into a first generator to receive and transduce said second electrical three-stimulus signal into a second acoustic three-stimulus signal, said first and second acoustic three-stimulus signals operative for stimulating an evoked otoacoustic emission response;

said probe assembly including an acoustic transducer to convert detected acoustic energy into an electrical response signal with said three-stimulus duration corresponding to said detected acoustic energy; and a processor coupled to said acoustic detector to receive said electrical response signal and to determine therefrom an evoked otoacoustic emission response;

said evoked otoacoustic emission response being calculated by the processor by partitioning said electrical response signal into a first-interval response signal in said first time interval, a second-interval response signal in said second time interval, and a third-interval response signal in said third time interval, and calculating said evoked otoacoustic emission response by subtracting said first-interval response signal and said second-interval response signal from said third-interval response signal.

19. The system of claim 18 wherein said signal generator includes a first and a second digital to analog converter to generate said first and said second electrical three-stimulus signal, respectively.

20. The system of claim 18 wherein said first arbitrary waveform sand said second arbitrary waveform are substantially identical.

21. The system of claim 18 wherein said first arbitrary waveform generated by said signal generator is characterized by a first amplitude, and said second arbitrary waveform having a waveform shape identical to said first arbitrary waveform except for a second amplitude with arbitrary value, and a relative delay time.

22. The system of claim 21 wherein said second amplitude and said first amplitude are substantially equal.

23. The system of claim 21 wherein said delay time ranges from 0 to 10 milliseconds.

24. The system of claim 18 wherein said first arbitrary waveform is a first transient arbitrary waveform and said second arbitrary waveform is a second transient arbitrary waveform.

25. the system of claim 24 wherein said first arbitrary waveform comprises a first short-duration, windowed sinusoidal tone of arbitrary first frequency, first amplitude and first phase joined to a first duration of zero amplitude, and in which said second arbitrary waveform comprises a second short-duration, windowed sinusoidal tone of arbitrary second frequency, second amplitude and second phase joined to a second duration of zero amplitude, and for which the durations of each of the first and second windowed sinusoidal tones and said first and second durations of zero amplitude are arbitrary subject to the constraint that the first and second arbitrary waveforms have the same said elementary duration.

26. The system of claim 25 in which said first frequency and said second frequency are equal.

27. The system of claim 18 wherein said first arbitrary waveform is continuous arbitrary waveform and said second arbitrary waveform is a transient arbitrary waveform.

28. The system of claim 18 wherein said first arbitrary waveform is a first continuous arbitrary waveform and said second arbitrary waveform is a second continuous arbitrary waveform.

29. The system of claim 28 wherein said first continuous arbitrary waveform is a continuous sinusoidal tone with a first frequency, first amplitude and first phase and said second continuous arbitrary waveform is a continuous sinusoidal tone with a second frequency, second amplitude and second phase.

30. The system of claim 29 in which said first frequency and said second frequency are equal.

31. The system of claim 18 wherein said first and second stimulus signals are first and second chirp signals, respectively, said first chirp having a first predetermined group delay, and said second chirp signal having a second predetermined group delay, said first and second predetermined group delays having a predetermined relationship.

32. The system of claim 31 wherein said second predetermined group delay is a predetermined multiple of said first predetermined group delay.

33. The system of claim 31 wherein said first and second chirp signals are linear chirp signals with said first and second group delays each being a linear function of frequency.

34. the system of claim 31 wherein said first and second chirp signals are logarithmic function of frequency.

35. The system of claim 31 wherein said first chirp signal is related to said second chirp signal such that each frequency of said second chirp signal at a given point in time is a fixed multiple of each frequency of said first chirp signal at said given point in time.

36. The system of claim 31 wherein said source transducer produces first and second acoustic chirp signals in response to said first and second chirp signals, respectively, said acoustic transducer detecting an acoustic chirp response signal from the ear in response to the first and second acoustic chirp signals and generating an electrical chirp response signal corresponding to said acoustic chirp response signal; and said processor being coupled to said acoustic transducer to receive said electrical chirp response signal and to determine therefrom an evoked cochlear response to said first and second acoustic chirp signals.

37. The system of claim 36 further including an inverse allpass filter within said processor to convert said electrical chirp response signal into a dechirped electrical response signal indicative of an equivalent cochlear response to click signals.

38. The system of claim 18 wherein said first and second stimulus signals are first and second click signals, respectively.

39. The system of claim 18 wherein the probe assembly contains a static pump that modifies the static pressure in the ear canal, and the evoked otoacoustic emission response is measured at one or more static pressures.

* * * * *